(12) United States Patent
Yin et al.

(10) Patent No.: US 12,291,600 B2
(45) Date of Patent: May 6, 2025

(54) THREE-DIMENSIONAL SPHERICAL ALPHA-HELIX CATIONIC POLYPEPTIDE HAVING HIGH-EFFICIENCY GENE DELIVERY CAPABILITY, AND PREPARATION METHOD AND APPLICATION THEREOF

(71) Applicant: SOOCHOW UNIVERSITY, Suzhou (CN)

(72) Inventors: Lichen Yin, Suzhou (CN); Huan Ye, Suzhou (CN); Rongying Zhu, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 724 days.

(21) Appl. No.: 17/797,398

(22) PCT Filed: Sep. 29, 2020

(86) PCT No.: PCT/CN2020/119113
§ 371 (c)(1),
(2) Date: Aug. 3, 2022

(87) PCT Pub. No.: WO2021/037281
PCT Pub. Date: Mar. 4, 2021

(65) Prior Publication Data
US 2023/0094088 A1 Mar. 30, 2023

(30) Foreign Application Priority Data
Aug. 30, 2019 (CN) .......................... 201910817961.4

(51) Int. Cl.
*C08G 69/48* (2006.01)
*A61K 9/51* (2006.01)
*C08G 69/16* (2006.01)

(52) U.S. Cl.
CPC ............ *C08G 69/48* (2013.01); *A61K 9/5146* (2013.01); *C08G 69/16* (2013.01)

(58) Field of Classification Search
CPC ....... C08G 69/48; C08G 69/16; A61K 9/5146
See application file for complete search history.

(56) References Cited

FOREIGN PATENT DOCUMENTS

| CN | 1891725 A | 1/2007 |
|----|-----------|--------|
| CN | 1911983 A | 2/2007 |

(Continued)

*Primary Examiner* — Trevor Love
(74) *Attorney, Agent, or Firm* — SZDC Law P C

(57) ABSTRACT

A three-dimensional star-shaped α-helix polypeptide having a high-efficiency gene delivery capability, and a preparation method and an application thereof. A dendrimer is used as an initiator and dichloromethane is used as a reaction solvent to initiate high-speed ring-opening polymerization of different types of N-carboxylic anhydride monomers, and groups having different electrical properties are introduced at the ends via click chemistry reactions. The abundant amino groups on the surface of the dendrimer provide enough polymerization sites to enable the polypeptide to form a three-dimensional spherical topological structure, and the topological structure provides an opportunity for initial acceleration of the ring-opening polymerization reaction. The higher positive charge density caused by polypeptide side chain modified guanidine/amino groups etc. achieves a high-efficiency gene loading capability by the electrostatic effect between positive and negative charges, and the α-helix rigid structure on the secondary structure thus enables the polypeptide to have stronger membrane penetration capability.

8 Claims, 6 Drawing Sheets

(56) References Cited

FOREIGN PATENT DOCUMENTS

| | | |
|---|---|---|
| CN | 102604013 A | 7/2012 |
| CN | 102936337 A | 2/2013 |
| CN | 108003343 A | 5/2018 |
| WO | 2018102774 A2 | 6/2018 |

THREE-DIMENSIONAL SPHERICAL ALPHA-HELIX CATIONIC POLYPEPTIDE HAVING HIGH-EFFICIENCY GENE DELIVERY CAPABILITY, AND PREPARATION METHOD AND APPLICATION THEREOF

This application is the National Stage Application of PCT/CN2020/119113, filed on Sep. 29, 2020, which claims priority to Chinese Patent Application No. 201910817961.4, filed on Aug. 30, 2019, which is incorporated by reference for all purposes as if fully set forth herein.

TECHNICAL FIELD

The invention relates to the field of gene loading and delivery, in particular to a three-dimensional spherical α-helical polypeptide with high gene delivery efficiency, a preparation method and application thereof, which can be applied to the photothermal-gene combined therapy of breast cancer.

BACKGROUND TECHNIQUE

Vectors delivered by gene are necessary media for loading nucleic acid molecules and introducing them into target cells and thus expressing them successfully. They are mainly divided into viral vectors and non-viral vectors. Viral vectors have been widely used because of their high efficiency in transduction and expression, but their development has been severely restricted by their antigenicity, potential tumorigenic risk and insufficient gene loading quantity. Therefore, non-viral vectors have gradually got attention. The commonly used non-viral vectors are liposomes, nanoparticles, cationic polymers and polysaccharides. α-helical polypeptides, especially cationic polypeptides, are novel and efficient gene delivery vectors. Although they belong to this type, the endocytosis mechanism of traditional polymers, these polypeptides mainly "punch holes" in the biofilm and penetrate cell membrane through the rigid secondary structure of the α-helix. However, when used at high doses or in contact with cells for a long time, polypeptides will punch too many holes in the biofilm, resulting in significant cytotoxicity.

Technical Problem

The present invention provides a three-dimensional topological structure of a star-shaped polypeptide, which is obtained by initiating ring-opening polymerization of N-carboxylic anhydride monomers with dichloromethane and N, N-dimethylformamide as the reaction solvents, respectively, and by small molecule modification. The abundant amino groups on the surface of the dendrimer provide enough polymerization sites for the polypeptide to form a three-dimensional spherical topology, and due to the low dielectric constant of dichloromethane, the topology formed at the beginning of the ring-opening polymerization promotes the acceleration of the later polymerization and greatly shortens the time required for polymerization. If positively charged groups such as guanidinium group and aromatic group are introduced into the side chain of polypeptide, it can improve the complexation ability of polypeptide with siRNA through hydrophobic interaction, and thus improve the gene silencing efficiency of polypeptide. If the negative charge group is introduced together, the in vivo circulation ability of polypeptide can be improved. In addition, α-helical cationic polypeptide can also "punch" on the lysosomal/intron membrane, so it can deliver nucleic acid molecules into the cell and escape from the intron/lysosome with high efficiency and low energy consumption to achieve efficient gene transfection.

Technical Solutions

In order to achieve the above-mentioned object of the invention, the technical solution adopted by the present invention is: A three-dimensional spherical α-helical polypeptide with high gene delivery efficiency has the chemical structure shown by Formula (I).

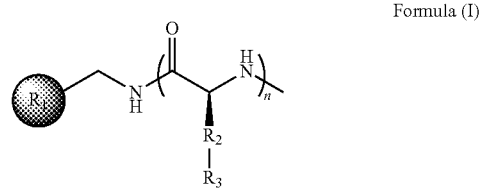

Formula (I)

In Formula (I), $R_1$ is a dendrimer polyacrylamide unit, $R_2$ is an N-carboxylic anhydride monomer unit, $R_3$ is an electrical small molecular unit.

A method of preparing the three-dimensional spherical α-helical polypeptide includes the following steps: the branched dendrimer polyacrylamide initiates the polymerization of an N-carboxyanhydride compound to obtain an intermediate; then the intermediate is reacted with an electrical small molecule to obtain the three-dimensional spherical α-helical polypeptide with high gene delivery efficiency.

The above method of preparing three-dimensional spherical α-helical polypeptide includes the following steps: (1) the branched dendrimer polyacrylamide with a structure of Formula (II), Formula (III), Formula (IV), or Formula (V) initiates the polymerization of the N-carboxyanhydride compound in an organic solvent to obtain the intermediate; the N-carboxyanhydride compound is γ-(4-propargyloxy-benzyl)-L-glutamic acid N-carboxyanhydride, γ-propargyl-L-glutamic acid N-carboxyanhydride, or N,N-benzyloxycarbonyl-L-lysine anhydride;

(2) The three-dimensional spherical α-helical polypeptide with efficient gene delivery capability is obtained by a click chemistry reaction of the intermediate with an electrical small molecule.

The present invention discloses an intermediate, and the preparation method thereof includes the following steps.

(1) A branched dendrimer polyacrylamide with a structure of Formula (II), Formula (III), Formula (IV), or Formula (V) initiates the polymerization of an N-carboxyanhydride compound in an organic solvent to obtain the intermediate; the N-carboxyanhydride compound is γ-(4-propargyloxyben-zyl)-L-glutamic acid N-carboxyanhydride, γ-propargyl-L-glutamic acid N-carboxyanhydride, or N,N-benzyloxycarbonyl-L-lysine anhydride.

In the present invention, in step (1), the reaction is conducted for 0.5-1 h at room temperature when the organic solvent is dichloromethane, and for 72 h at room temperature when the organic solvent is N, N-dimethylformamide; in step (2), the click chemistry reaction is catalyzed by pentamethyldiethylenetriamine and cupric bromide, and the reaction is conducted at room temperature for 24 h.

The present invention discloses a nano-medicine including a three-dimensional spherical α-helical polypeptide with efficient gene delivery capability and a nucleic acid molecule. The nucleic acid molecule is a DNA, an RNA, an oligonucleotides or a polynucleotide. Further, the nano-medicine also includes other drugs, such as indocyanine green.

The present invention also discloses a method for the preparation of a nano-medicine that includes the steps of dissolving the aforementioned three-dimensional spherical α-helical polypeptide with efficient gene delivery capability in DEPC water, then mixing it with a nucleic acid solution, and then incubating it in 37° C. water bath for 30 min to obtain the nano-medicine. The nucleic acid drug is selected from the group consisting of a DNA, an RNA, an oligonucleotide or a polynucleotide. Preferably, the DNA is a plasmid DNA, which can express proteins or transcribe into a small molecule of interfering RNA.

In some embodiment, a mass ratio of the three-dimensional star-shaped α-helical polypeptide to the nucleic acid molecule is (1 to 30):1; preferably, the mass ratio is (8 to 20):1; more preferably (10 to 15):1. The particle size of the drug is from 100 to 1000 nm; preferably, the particle size is 100 to 500 nm; more preferably 100 to 150 nm. The zeta potential of the drug is from −20 to 70 mV.

The present invention also discloses an application of the intermediate in the preparation of the three-dimensional spherical alpha helical cationic polypeptide with efficient gene delivery capability or in the preparation of a carrier for a nano-medicine.

The present application also discloses an application of the three-dimensional spherical alpha helical cationic polypeptide with efficient gene delivery capability in the preparation of a nucleic acid drug carrier; or an application of the three-dimensional spherical alpha helical cationic polypeptide with efficient gene delivery capability in the preparation of a gene drug. Preferably, the gene drug is a drug for the treatment of breast cancer.

The chemical structure of the groups, compounds or polymers of the present invention are as follows:

The chemical structure of γ-(4-propargyloxybenzyl)-L-glutamic acid N-carboxyanhydride is:

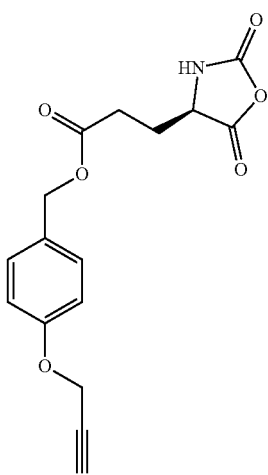 [SMILES: C#CCOc1ccc(COC(=O)CC[C@H]2NC(=O)OC2=O)cc1]

The chemical structure of γ-propargyl-L-glutamic acid N-carboxyanhydride is:

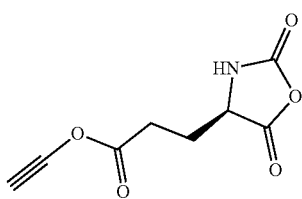

The chemical structure of N,N-benzyloxycarbonyl-L-lysine anhydride is:

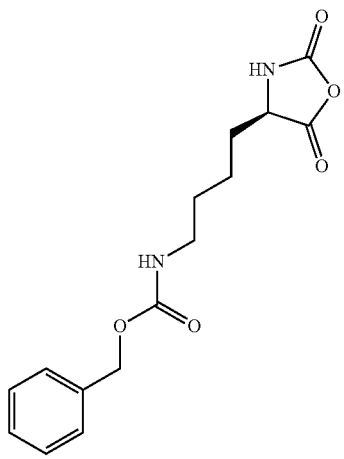 [SMILES: O=C(NCCCC[C@H]1NC(=O)OC1=O)OCc1ccccc1]

In step (2), the chemical structure of the electrical small molecule is one of the followings.

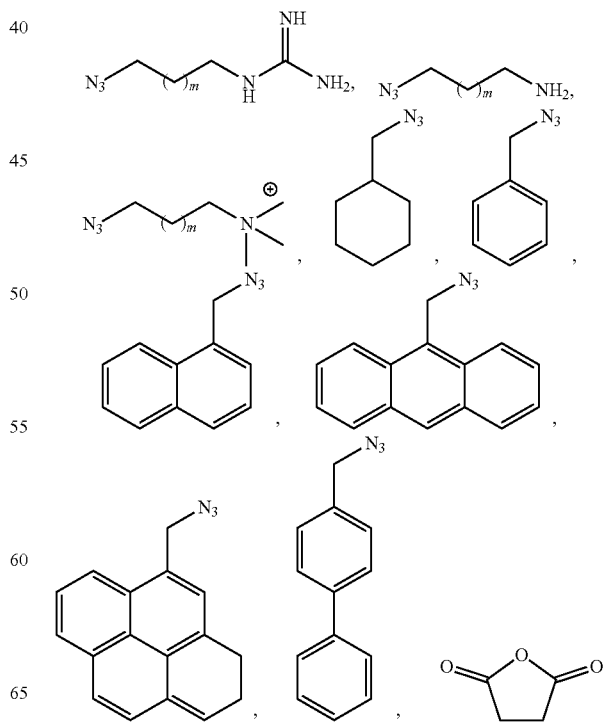

The chemical structure of the intermediate is:
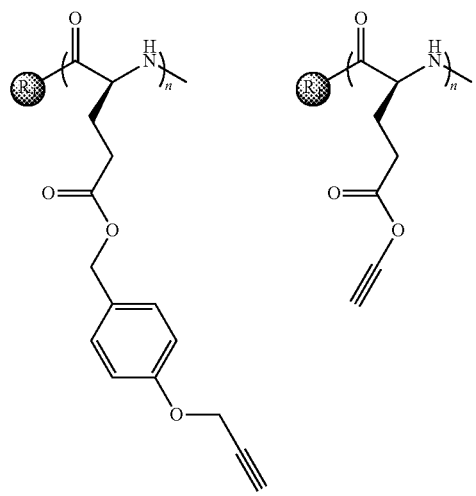
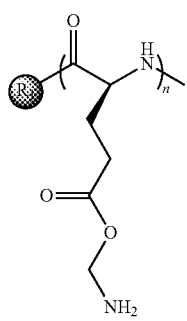
The chemical structure of the dendrimer polyacrylamide is:
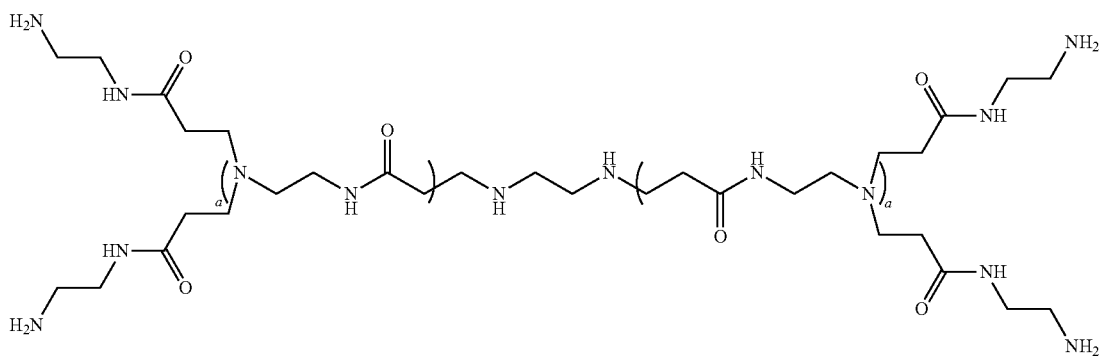
Wherein a is 2 to 8, preferably 2, 3, 4, 5.
Specifically, the first generation of the dendritic molecule is:
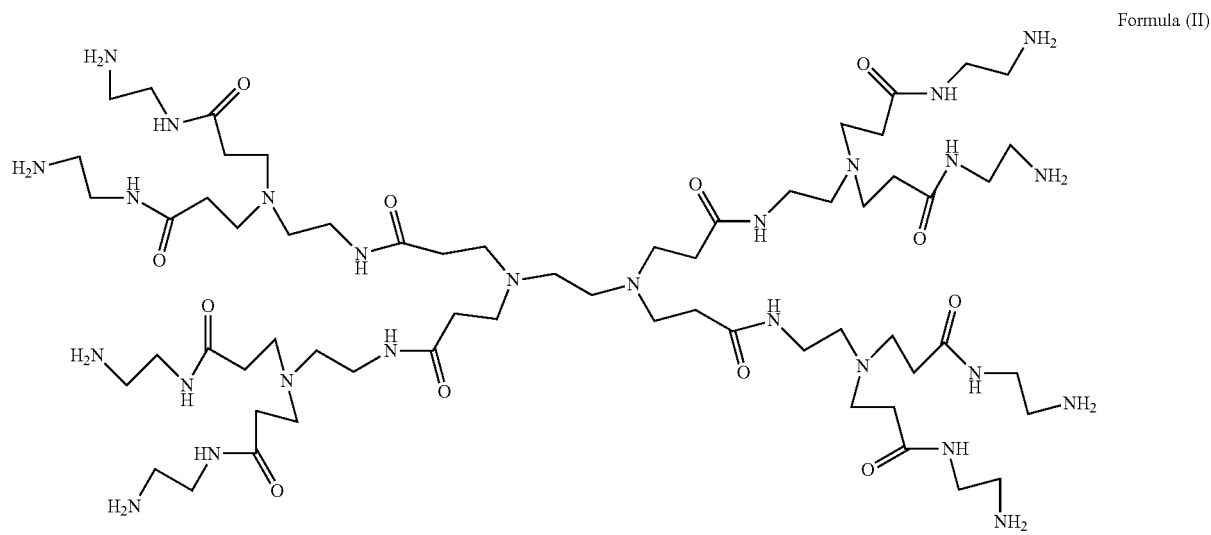 [SMILES: NCCNC(=O)CCN(CCNC(=O)CCN(CCC(=O)NCCN(CCC(=O)NCCN)CCC(=O)NCCN)CCN(CCC(=O)NCCN(CCC(=O)NCCN)CCC(=O)NCCN)CCC(=O)NCCN(CCC(=O)NCCN)CCC(=O)NCCN)CCC(=O)NCCN]
Formula (II)

The second generation of the dendritic molecule is:
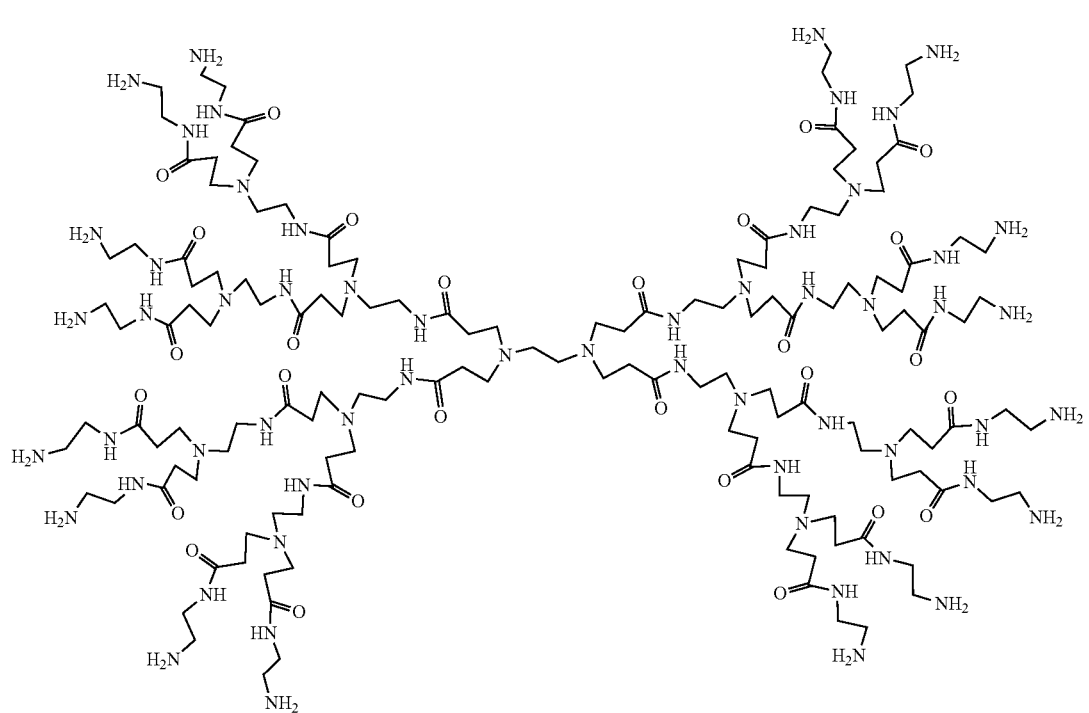
Formula (III)
The third generation of the dendritic molecule is:

Formula (VI)
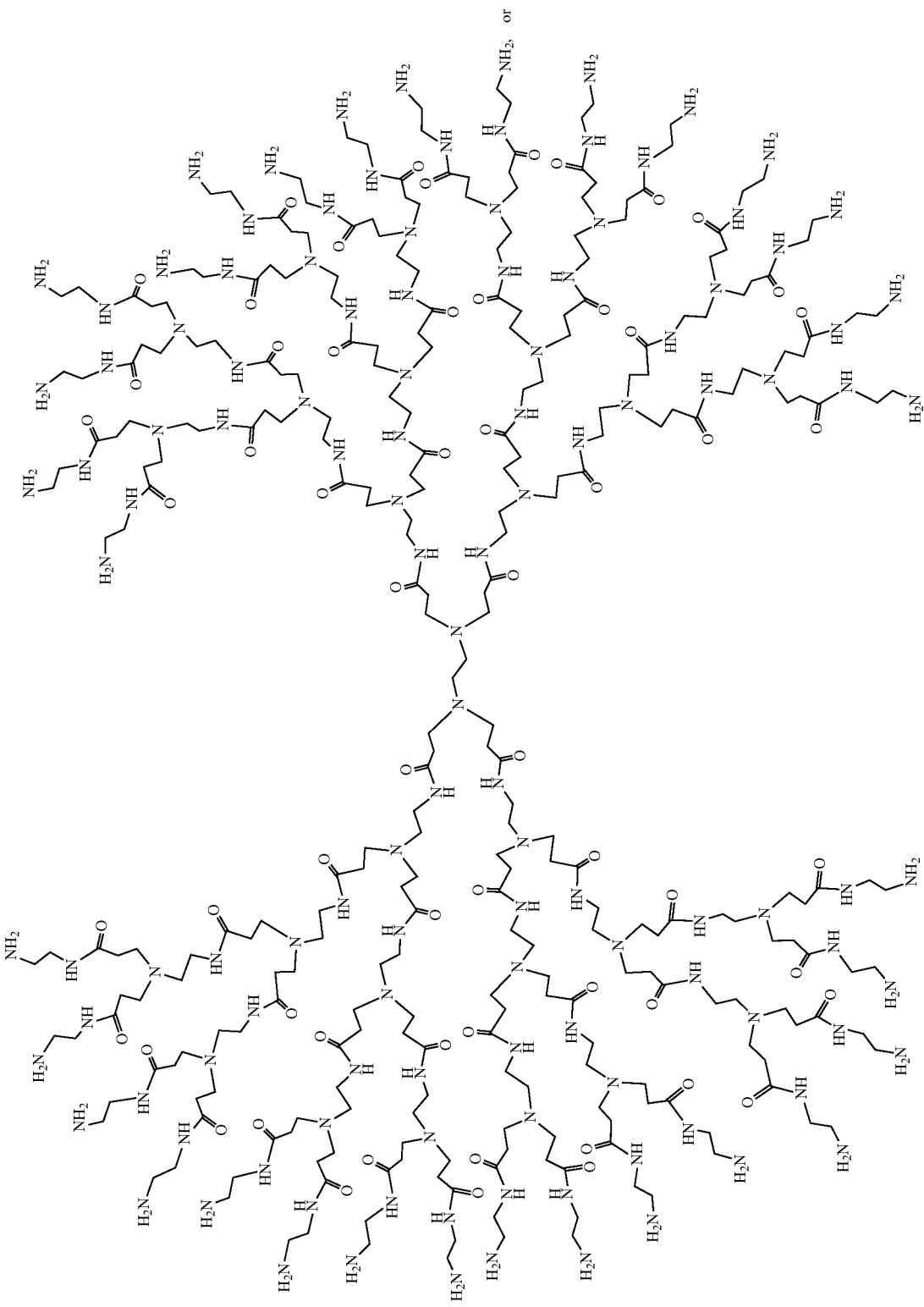
, or

The fourth generation of the dendritic molecule is:

Formula (V)
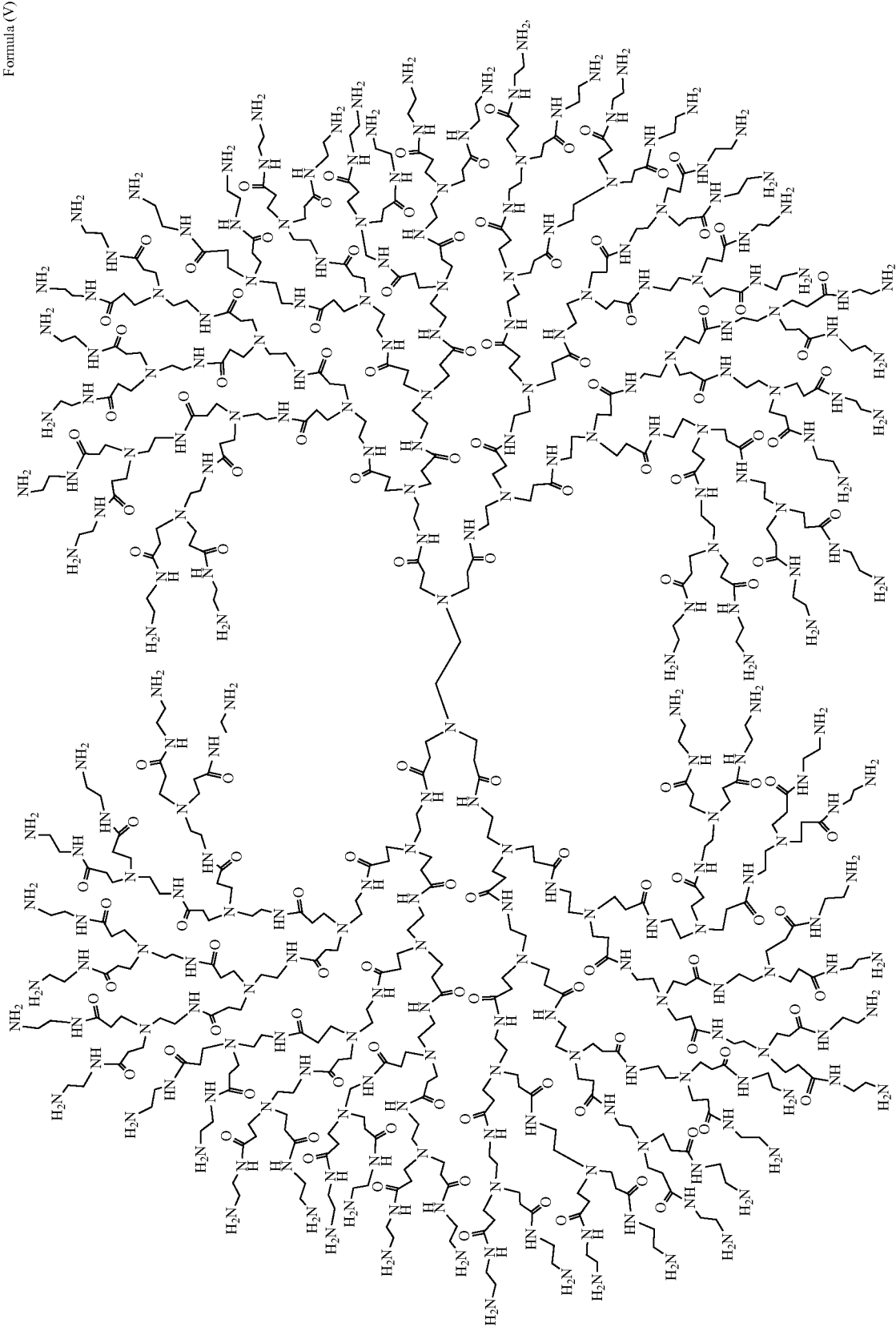

The N-carboxylic anhydride monomer unit is derived from the ring-opening polymerization of different kinds of N-carboxylic anhydride monomers with one of the following structural formulas specifically:

Formula (VI)

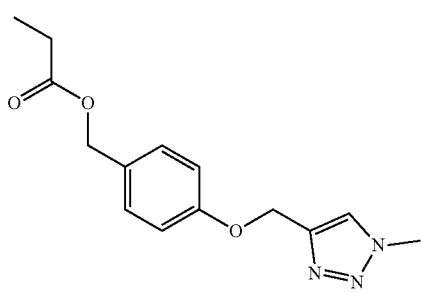

Formula (VII)

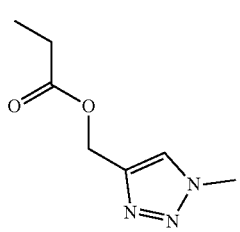

Formula (VIII)

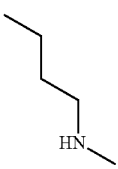

The electrical small molecule unit is selected from one of the following moieties:

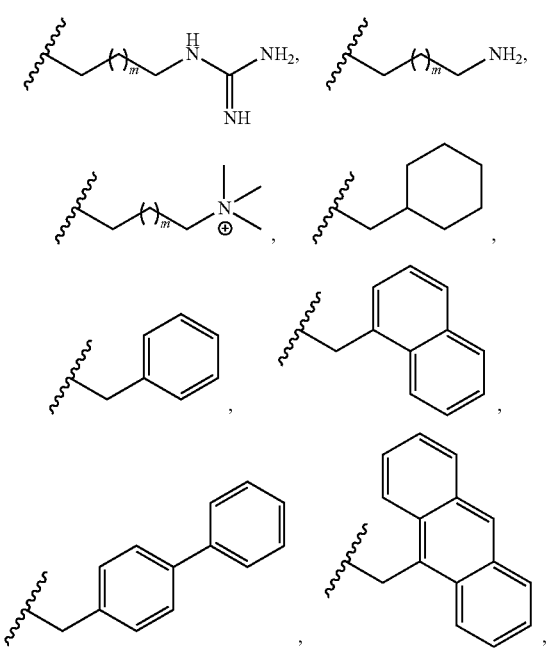

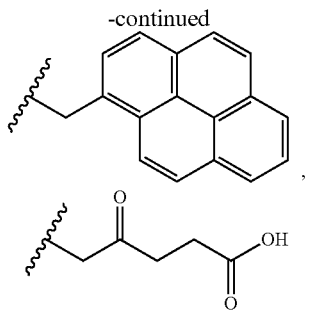

In the present invention, n represents the number of repeating units of the polypeptide backbone, i.e. the degree of polymerization, and n is from 20 to 200, e.g., n=20, 50, 100, 200; m is from 1 to 6, for example, m=1, 4, 6.

The polypeptide designed in this invention can introduce different electrical groups at the end by click chemistry reaction, in which the three-dimensional spherical α-helical cationic polypeptide, the abundant amino groups on the surface of dendritic molecules provide enough polymerization sites, so that the polypeptide forms a three-dimensional spherical topology, and the topology provides an opportunity to accelerate the ring-opening polymerization reaction at the beginning. The side chain modified guanidine group of polypeptide brings higher positive charge density, which can obtain efficient gene loading ability through electrostatic interaction between positive and negative charges, and enhances the α-helical rigid structure on the secondary structure and thus has stronger membrane penetration ability.

The present invention also provides a detailed method for the preparation of three-dimensional spherical α-helical polypeptides having the structure of formula (I), as follows:

① Preparation of copper(II) L-glutamate complexes from L-glutamic acid and hydrated copper acetate;

Preparation of γ-(4-propynyloxybenzyl)-L-glutamic acid-N-carboxylic anhydride monomer from p-hydroxybenzyl alcohol, bromopropyne, sulfoxide chloride, L-glutamic acid copper (II) complex and bis(trichloromethyl) carbonate.

② Preparation of azidoguanidine based small molecules from 1,6-dibromohexane, sodium azide, triphenylphosphine and 1H-pyrazole-1-carboxamidine hydrochloride.

③ Preparation of three-dimensional spherical α-helical cationic polypeptides from third-generation dendrimer polyacrylamide, γ-(4-propyloxybenzyl)-L-glutamic acid-N-carboxylic anhydride monomer and azide-guanidine small molecule.

The above method of preparing three-dimensional spherical α-helical cationic polypeptides with high gene delivery capacity can be exemplified as follows.

① Added aqueous copper acetate solution dropwise to aqueous L-glutamic acid solution, let it stand and then wash the precipitate with water, ethanol and petroleum ether in turn with stirring, and then extracted the blue solid, i.e., L-glutamic acid copper (II) complex.

Bromopropyne and 18-crown-6 were Added to a solution containing potassium carbonate and p-hydroxybenzyl alcohol, and the solvent was removed after reflux reaction, then water was Added, and then extracted with dichloromethane, and the organic phase obtained was washed with aqueous sodium hydroxide solution and then dried, filtered and spun to give compound 1.

Under the condition of ice bath, added sulfoxide chloride to the dichloromethane solution of compound 1, stir the reaction at room temperature and then wash with water, the organic phase obtained is dried, filtered and spun off to obtain compound 2.

Compound 2 was Added to a mixture of L-glutamic acid copper (II) complex, L-glutamic acid, DMF, water, and 1, 1, 3, 3-tetramethylguanidine, and the reaction was stirred at room temperature, then acetone was Added, and the solids were centrifuged after stirring again to obtain solids; the solids were sequentially washed with acetone, washed with water, and washed with disodium EDTA and Added to a mixture of isopropanol and water, then compound 3 was obtained by hot filtration.

The (trichloromethyl) carbonate was Added to anhydrous tetrahydrofuran solution of compound 3, and the solvent was removed under vacuum after reflux reaction, and the residue was recrystallized to obtain γ-(4-propyloxybenzyl)-L-glutamic acid-N-carboxylic anhydride monomer.

② 1, 6-dibromohexane and sodium azide were dissolved in DMF and reacted at 60° C. for 24 h. Subsequently, water was Added, and the organic phase was extracted with ether and collected, and then the organic phase was dried with sodium sulfate, filtered and spun to obtain a white oily substance, i.e., compound 4.

Dissolved compound 4 in a mixture of ether and ethyl acetate, and added hydrochloric acid solution, then Added triphenyl phosphorus under ice bath conditions, and wash with hydrochloric acid solution after the reaction, and collecting the aqueous phase after partitioning; extracted the aqueous phase with dichloromethane, then adjust the collected lower aqueous phase with sodium hydroxide pH≥12, then extracted with dichloromethane and collecting the organic phase, and Added sodium sulfate to dry the organic phase and filter and spin to obtain compound 5.

The mixture of compound 5, 1H-pyrazole-1-carboxamidine hydrochloride, anhydrous N,N-dimethylformamide, and N, N-diisopropylethylamine was reacted at room temperature with stirring and then Added to ether, and then the precipitate was collected by centrifugation, and then the ether was poured off after vortex shaking of the precipitate with ether, and the solvent was removed to obtain azidoguanidine small molecules, i.e., electrical small molecules.

③ In a glove box, γ-(4-propyloxybenzyl)-L-glutamic acid-N-carboxylic anhydride monomer is dissolved in organic solvent and dendrimer is Added, and the reaction phase is Added dropwise to ice methanol after stirring the reaction at room temperature, and then the methanol is removed by centrifugation to obtain polymer A; preferably, the organic solvent is anhydrous N,N-dimethylformamide or anhydrous dichloromethane; further preferably, the reaction time is 30 min with stirring at room temperature when the organic solvent is anhydrous dichloromethane, and 72 h with stirring at room temperature when the organic solvent is N,N-dimethylformamide.

In a glove box, polymer A was dissolved in anhydrous N,N-dimethylformamide, guanidine small molecules, N, N, N', N, 'N'''-pentamethyldiethylenetriamine and cuprous bromide were Added, and the reaction vial was removed from the glove box after stirring the reaction at room temperature, 1 M hydrochloric acid solution was Added and stirred, preferably for 30 min; then the reaction phase was dialyzed with water (molecular weight of dialysis bag was 3.5 kDa, and Then the reaction phase was dialyzed with water (dialysis bag with molecular weight of 3.5 kDa, dialyzed for 3 days) and lyophilized to obtain three-dimensional spherical α-helical cationic polypeptide with structure of formula (I).

The specific reactions described above (the raw materials involved as well as the products of each step) can be expressed as follows:

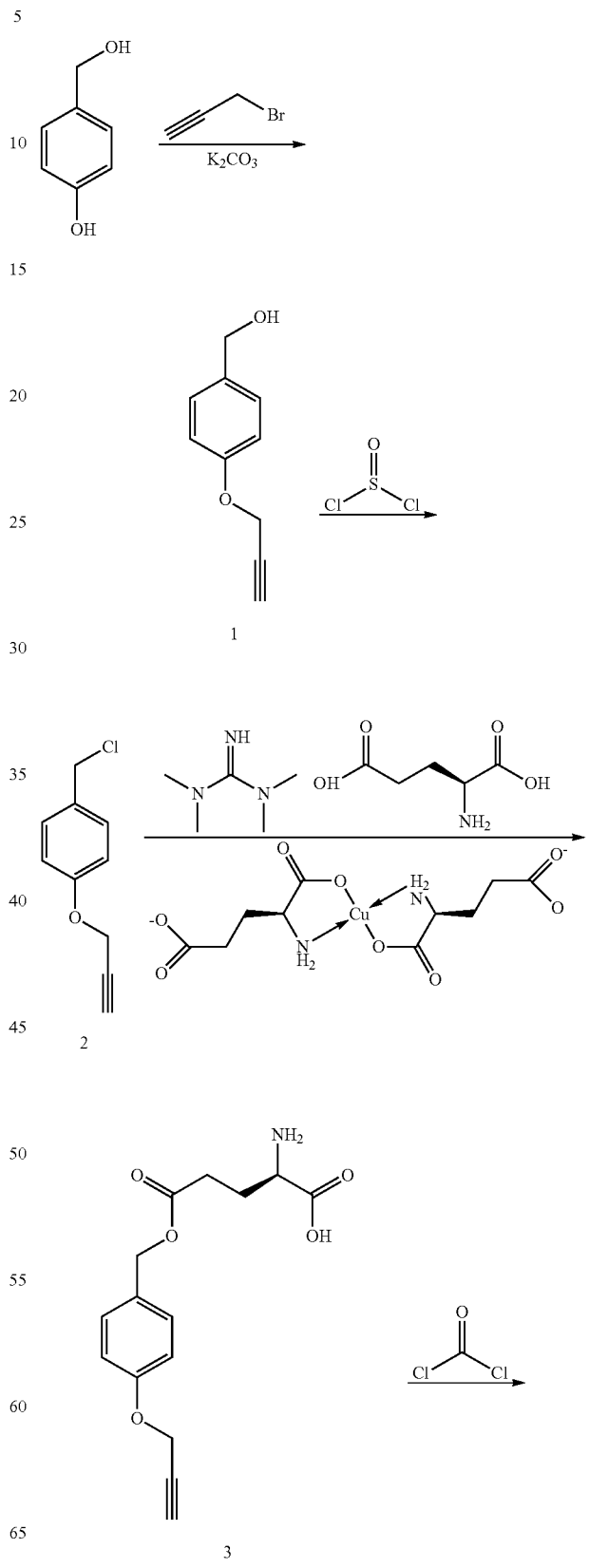

-continued

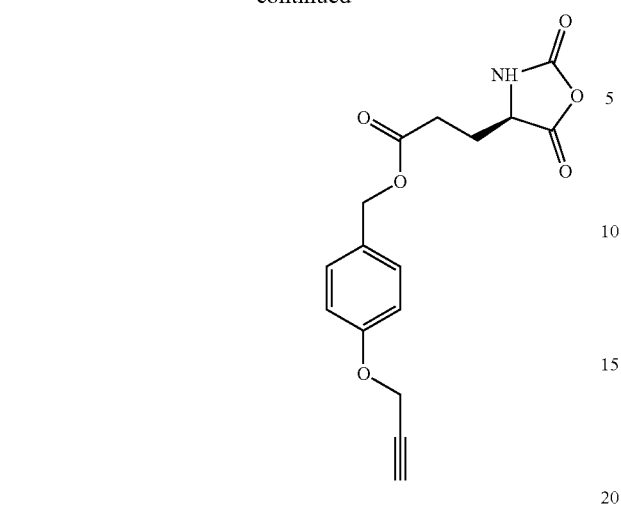

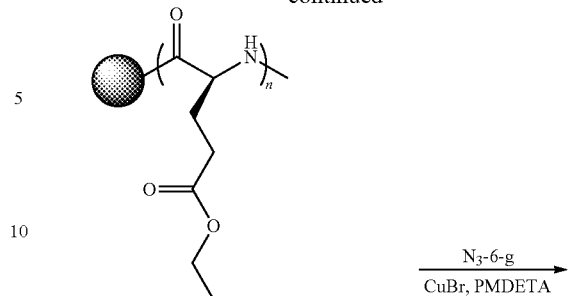

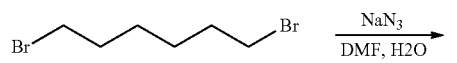

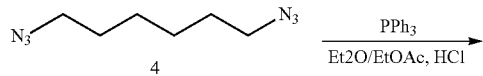

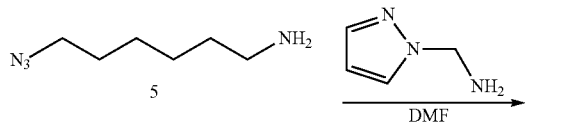

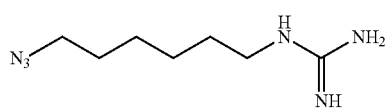

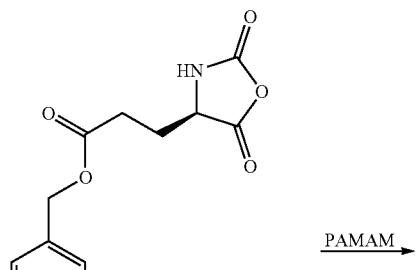

The cationic polypeptide of α-helical conformation with three-dimensional spherical topology containing guanidine group in the side chain provided by the present invention can self-assemble with nucleic acid drug to form nanoparticles, which consist of positively charged α-helical conformation of cationic polypeptide and negatively charged nucleic acid drug, so the present invention also discloses a nanomedicine including α-helical cationic polypeptide with nucleic acid drug. The polypeptide of the present invention can not only encapsulate genes to form a drug, but also co-encapsulate genes with other drugs to form a composite nanodrug, other drugs such as dyes, specifically indocyanine green, etc.

Beneficial Effects

The main advantages of the present invention are, (1) Dendrimers as initiators have the following advantages: dendrimers act as hydrophobic internal cavities and can be used to embed hydrophobic small molecules; dendrimers with 8, 16, 32 and 64 amino groups at the end of different generations of dendrimers provide abundant sites for the formation of polypeptides with 3D spherical topology.

(2) The present invention uses dichloromethane, which has a small dielectric constant, as the solvent, and finds that at the initial stage of forming a three-dimensional spherical topology on the surface of dendritic molecules, the close proximity between polypeptide chains forces them to grow faster outward, and in addition, when the polypeptide chains form an α-helical conformation, the hydrogen bonding network generates a great dipole moment along the helical axis, which accelerates the propagation rate of ring-opening polymerization.

(3) The cationic polypeptide of the present invention has higher positive charge density on its three-dimensional surface, which can compress and protect nucleic acid molecules more tightly when they are adsorbed. In addition, the three-dimensional spherical topology with high charge density and more rigid α-helical conformation helps to interact with cell membrane to improve the membrane penetration activity and delivery of nucleic acid molecules into the cell and more efficient escape of intron/lysosome, which makes it have high efficiency of gene transfection and low cytotoxicity.

DESCRIPTION OF DRAWINGS

FIG. 6 shows the polymerization rate of polymer A in Example 3; wherein FIG. 6A shows the polymerization rate of polymer A (M/I=20, 50, 100, 200, 400) at a starting concentration of 50 mM of γ-(4-propyloxybenzyl)-L-glutamic acid-N-carboxylic anhydride monomer in Example 3; FIG. 6B shows the polymerization rate of polymer A (M/I=20, 50, 100, 200, 400) at a starting concentration of 100 mM of γ-(4-propyloxybenzyl)-L-glutamic acid-N-carboxylic anhydride monomer in Example 3. (M/I=20, 50, 100, 200, 400) at the starting concentration of γ-(4-propyloxybenzyl)-L-glutamic acid-N-carboxylic anhydride monomer of Example 3 at 100 mM, respectively;

FIG. 7A shows the GPC spectra of polymers in Control Example 1 (M/I=20, 50, 100, 200); FIG. 7B shows the GPC spectra of polymer A in Control Example 3 (M/I=20, 50, 100, 200), HG indicates: polymer in Control Example 1; GG indicates: polymer A in Control Example 3;

FIG. 8A shows the particle size diagram of cationic polypeptide in Control Example 1 (M/I=20, 50, 100, 200); FIG. 8B shows the particle size diagram of cationic polypeptide in Example 3 (M/1=20, 50, 100, 200), L indicates cationic polypeptide in Control Example 1, D indicates cationic polypeptide in Example 3;

FIG. 17 shows the results of animal experiments, in which FIG. 17A is a diagram of gene transfection in female Balb/C mice bearing MCF-7 tumor in situ; FIG. 17B is heat shock in female Balb/C mice bearing MCF-7 tumor in situ Protein expression map; HSP70, HSP90 represent: two heat shock proteins; GAPDH represents: glutathione.

DETAILED DESCRIPTION

The ring-opening polymerization of γ-(4-propargyloxybenzyl)-L-glutamic acid N-carboxy anhydride monomer was prepared using hexamethyldisilylamine as initiator and N,N-dimethylformamide as reaction solvent, and the two-dimensional linear α-helical cationic polypeptide was obtained by guanidinium-based small molecule modification as a positive control for the three-dimensional spherical α-helical cationic polypeptide in the present invention.

Example 1

L-Glutamic acid (375 mL) was dissolved in water, stirred and heated to 70° C., then aqueous solution of copper acetate hydrate (18.6 g, 103 mmol) (375 mL) was dropped into the L-glutamic acid solution. After the stirring was stopped, the precipitate was washed by water, ethanol and petroleum ether for 24 h at room temperature, and the blue solid was obtained by filtration, freeze-dried and stored in a desiccator to obtain copper (II) L-glutamate complex.

Figure 1:
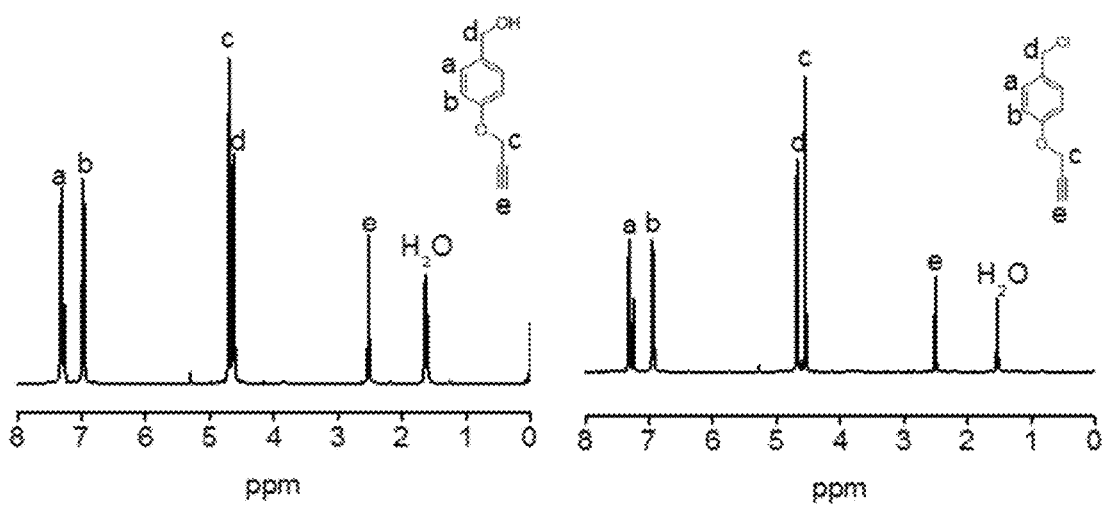
FIG. 1 shows the $^1$H NMR of compound 1 and compound 2 in Example 1 when deuterated chloroform is used as the solvent in Example 1.

Potassium carbonate (15.2 g, 0.11 mol) and p-hydroxybenzyl alcohol (9.3 g, 0.075 mol) were dissolved in acetone (150 mL), and bromopropyne (6.75 mL, 0.09 mol) and 18-crown were added to the solution Ether-6 (0.1 g). After the solution was refluxed and reacted at 75° C. for 12 h, the acetone was removed by a rotary evaporator, and water (200 mL) was added to dissolve the remaining solids. Extracted the solution with dichloromethane (30 mL×3) and combine the organic phases. After washing the organic phase with 15% sodium hydroxide (200 mL) and water (200 mL), sodium sulfate was added for drying. The solution was filtered and rotary evaporated to give compound 1, which was subjected to deuterated chloroform by $^1$H NMR. FIG. 1 shows the $^1$H NMR.

Compound 1 (8.5 g, 52 mmol) was dissolved in dichloromethane, thionyl chloride (6 mL, 68 mmol) was slowly added dropwise in an ice bath, and then the reaction was stirred at room temperature for 3.5 h. After the reaction was complete, water (100 mL) was added to quench the remaining thionyl chloride, and wash the organic phase with water (50 mL×3). After adding magnesium sulfate to dry the organic phase, filtering and rotary evaporation to remove the dichloromethane to obtain compound 2, deuterated chloroform was used for NMR. FIG. 1 shows the $^1$H NMR.

Figure 2:
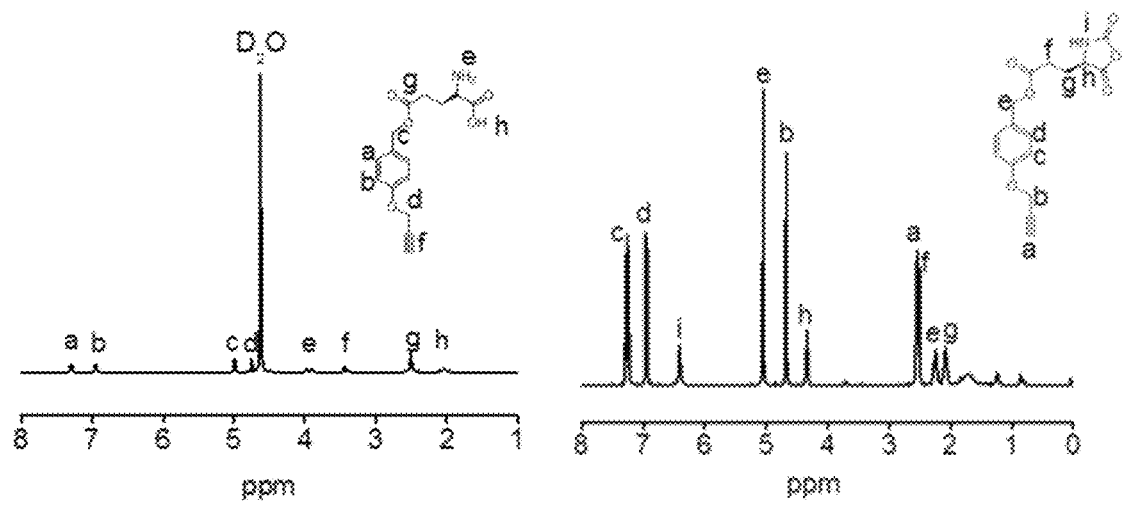
FIG. 2 shows the $^1$H NMR of compound 3 with deuterium oxide and γ-(4-propargyloxybenzyl)-L-glutamic acid N-carboxyanhydride as the solvent Example 1.

L-glutamate copper (II) complex (3.29 g, 6.7 mmol) and L-glutamic acid (1.99 g, 13.4 mmol) were added into a mixed solution of DMF (12 mL) and water (2 mL), and 1, 1, 3, 3-tetramethylguanidine (3.4 mL, 27 mmol) was added and stir at 40° C. for 2 h until the solid is dissolved. Then DMF (10 mL) and compound 2 (6.5 g, 36 mmol) were added, and the reaction was stirred at room temperature for 48 h. Next, acetone (200 mL) was added, and after stirring overnight at room temperature, the crude product was obtained by centrifugation (5000 rpm, 5 min, 25° C.). The crude product was washed 4 times with acetone (until the supernatant was no yellow), washed 3 times with water (until the supernatant was no blue), and washed 2 times with disodium edetate. Subsequently, the product was added to a mixed solution of isopropanol and water (isopropanol:water=2:1), heated to 80° C., and hot filtered to get the final product compound 3. NMR spectroscopy is shown in FIG. 2 for deuterium oxide.

Compound 3 (1.15 g, 4.0 mmol) was dissolved in anhydrous tetrahydrofuran (25 mL), then (trichloromethyl) carbonate (0.52 g) was added, and the reaction was refluxed at 50° C. for 2 h. Then the solvent was removed under vacuum, and the crude product was recrystallized three times (tetrahydrofuran:n-hexane=1:5) to obtain γ-(4-propargyloxybenzyl)-L-glutamic acid N-carboxyanhydride, deuterated chloroform NMR, FIG. 2 shows the $^1$H NMR.

Example 2

Figure 3:
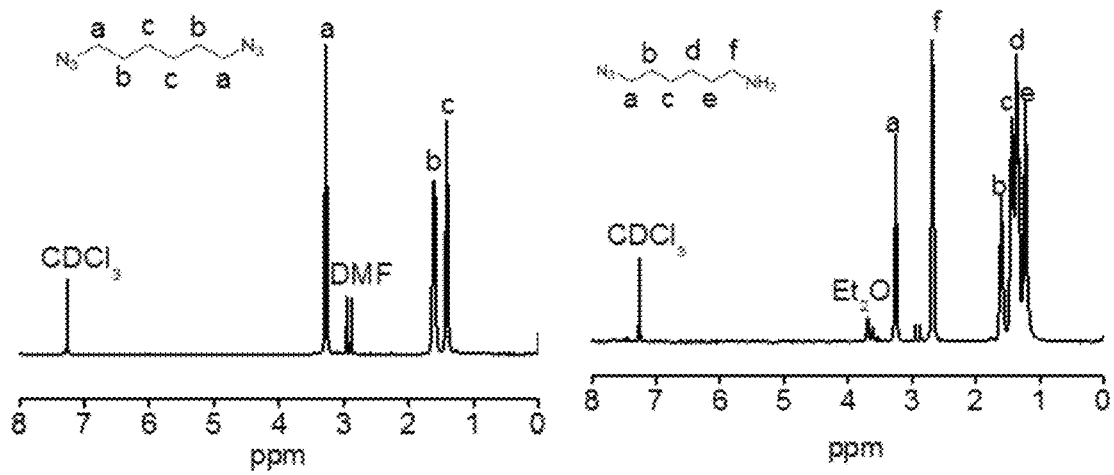
FIG. 3 shows the $^1$H NMR of compound 4 and compound 5 in Example 1 when deuterated chloroform is used as the solvent in Example 2.

1,6-Dibromohexane (1.26 mL, 8 mmol) and sodium azide (1.6 g, 24 mmol) were dissolved in DMF (19 mL), and reacted at 60° C. for 24 h. Then added water (150 mL) to the insoluble matter, extracted with ether (20 mL×3) to collect the organic phase. After the organic phase was dried with sodium sulfate, filtered and rotary steamed to obtain a white oily substance, called compound 4, deuterated chloroform by NMR. FIG. 3 shows the $^1$H NMR.

Compound 4 (3.33 g, 20 mmol) was dissolved in a mixed solvent of ether (15 mL) and ethyl acetate (15 mL), added 5% hydrochloric acid solution (30 mL), and slowly added triphenylbenzene under ice bath conditions Phosphorus (5.51 g, 22 mmol), ensure the separation of the two phases and slowly stir the reaction for 1 h, then reacted at room temperature for 24 h. Subsequently, 1M hydrochloric acid solution (30 mL) was added to wash the organic phase, and the aqueous phase was collected after stratification occurred. The aqueous phase was extracted with dichloromethane (20 mL×3), and the lower aqueous phase was collected. Then adjust the aqueous phase with sodium hydroxide to make the pH≥12, then extracted with dichloromethane (20 mL×4) and collecting the organic phase. After adding sodium sulfate to dry the organic phase, filtering and rotary evaporation to obtain compound 5, deuterated chloroform NMR, FIG. 3 shows the $^1$H NMR.

Figure 4:
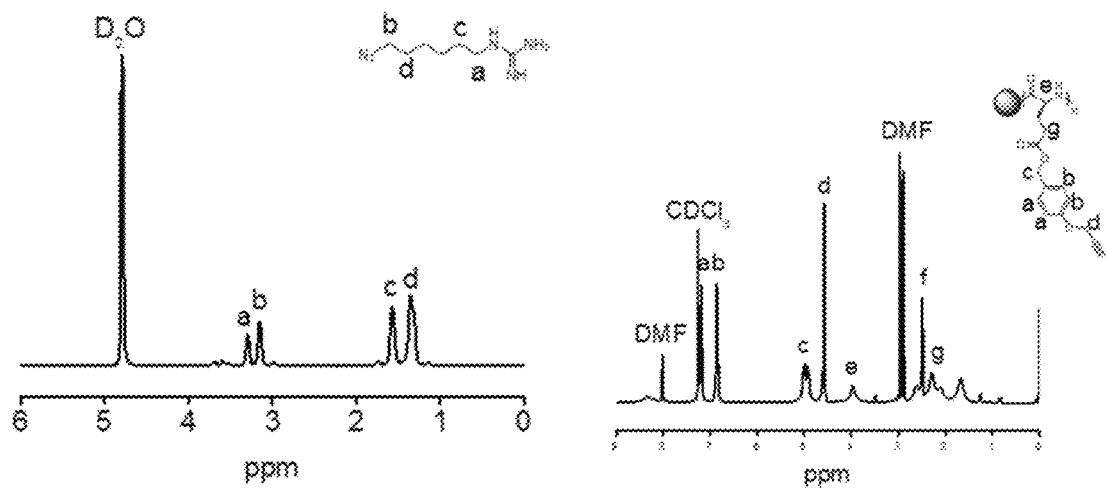
FIG. 4 shows the $^1$H NMR of the azide-guanidine based small molecule in Example 2 when deuterium oxide is used as the solvent, and the $^1$H NMR of polymer A in Example 3 when deuterated chloroform is used as the solvent.

Compound 5 (1.42 g, 10 mmol), 1H-pyrazole-1-carboxamidine hydrochloride (1.47 g, 10 mmol) were dissolved in anhydrous N,N-dimethylformamide (15 mL), and added N, N-Diisopropylethylamine (1.74 mL, 10 mmol) was stirred at room temperature for 24 h. Ether (150 mL) was added to precipitate the product and collecting it in a centrifuge tube. Ether was added again and vortex for a few minutes. Pour out the ether. Repeat until the solution is clear. After removing the solvent, a small molecule of guanidine azide group is obtained. FIG. 4 is its $^1$H NMR.

Example 3

In a glove box, γ-(4-propargyloxybenzyl)-L-glutamic acid N-carboxyanhydride monomer (50 mg, 1.6 mmol) was dissolved in anhydrous N,N-dimethylformaldehyde. The third generation dendrimer (0.68 mg, 0.001 mmol) was added to the amide (1 mL), and the reaction was stirred at room temperature for 72 h. Subsequently, the reaction phase was added dropwise to ice methanol (50 mL) to precipitate. After centrifugation, the methanol was removed to obtain polymer A. Deuterated chloroform was subjected to 1H NMR. FIG. 4 shows the $^1$H NMR.

Figure 8:
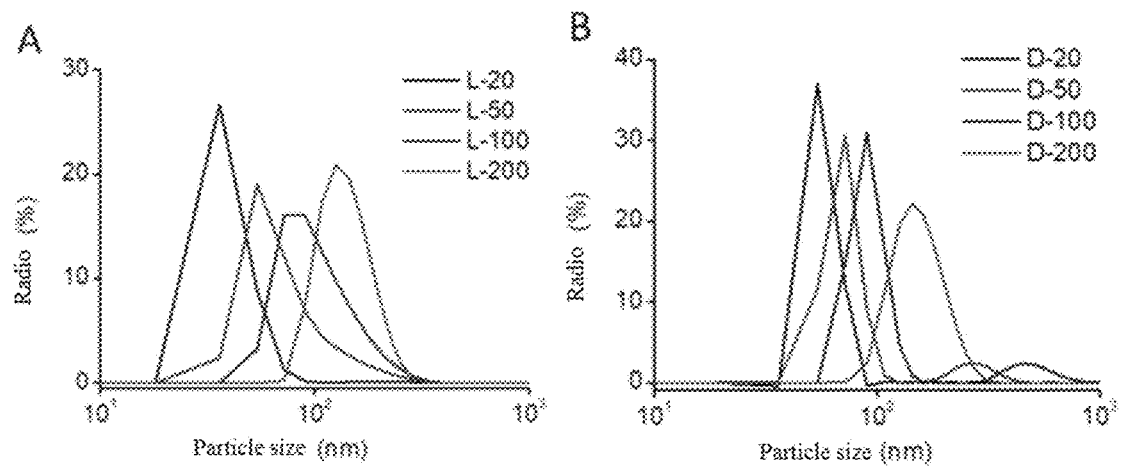
FIG. 8 shows the particle size diagram of cationic polypeptide, where

In a glove box, γ-(4-propargyloxybenzyl)-L-glutamic acid N-carboxyanhydride monomer (50 mg, 1.6 mmol) was dissolved in dry dichloromethane (1 mL), and the third generation dendrimer (0.68 mg, 0.001 mmol) was added, stirred and reacted at room temperature for 30 min. Subsequently, the reaction phase was added dropwise to ice methanol (50 mL) to precipitate. After centrifugation, the methanol was removed to obtain polymer A. Deuterated chloroform was used for NMR. FIG. 8 shows the $^1$H NMR. The number average molecular weight of polymer A is 190. kg/mol, M/I=50, used in the following cell experiments and animal experiments.

In a glove box, polymer A (20 mg, 0.001 mmol) was dissolved in anhydrous N,N-dimethylformamide (1 mL), small guanidine molecules (12 mg, 1.6 mmol), N, N,N', N,'N"-pentamethyldiethylenetriamine (10 μL) and cuprous bromide (5.2 mg) were added and stirred at room temperature for 24 h. Then remove the reaction flask from the glove box, 1M hydrochloric acid solution (1 mL) was added and stirred for 30 min. The reaction phase was dialyzed with water for 3 days (the molecular weight of the dialysis bag is 3.5 kDa) and then lyophilized to obtain a three-dimensional spherical α-helical cationic polypeptide. Deuterated trifluoroacetic acid:heavy water=9:1 (v:v) and NMR, shown in FIG. 5 1H NMR spectroscopy.

Figure 5:
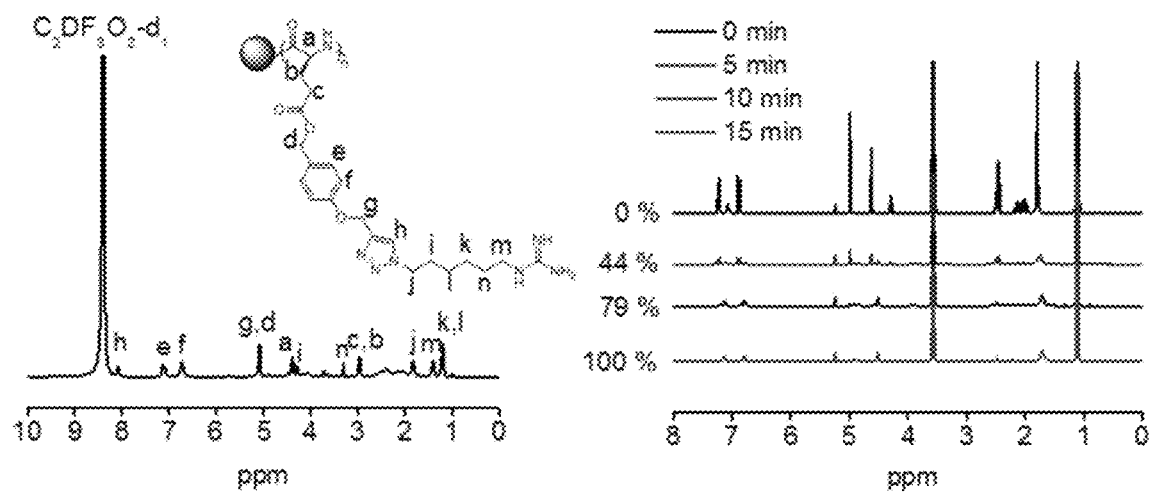
FIG. 5 shows the $^1$H NMR of the three-dimensional spherical α-helical polypeptide in Example 3 with deuterated trifluoroacetic acid:deuterium oxide=9:1 (v:v) as solvent; and the $^1$H NMR of polymer A (M/I=50) in Example 3 at a starting concentration of 50 mM of γ-(4-propyloxybenzyl)-L-glutamic acid-N-carboxylic anhydride monomer.

FIG. 5 shows the $^1$H NMR of the three-dimensional spherical α-helical polypeptide in Example 3 with deuterated trifluoroacetic acid:deuterium oxide=9:1 (v:v) as solvent; and the $^1$H NMR of polymer A (M/I=50) in Example 3 at a starting concentration of 50 mM of γ-(4-propyloxybenzyl)-L-glutamic acid-N-carboxylic anhydride monomer; according to the chart, the nitrogen and hydrogen proton peak on the monomer five-membered ring disappeared (7.06 ppm) within 15 minutes, and a new amide proton peak (6.76 ppm) appeared.

Figure 6:
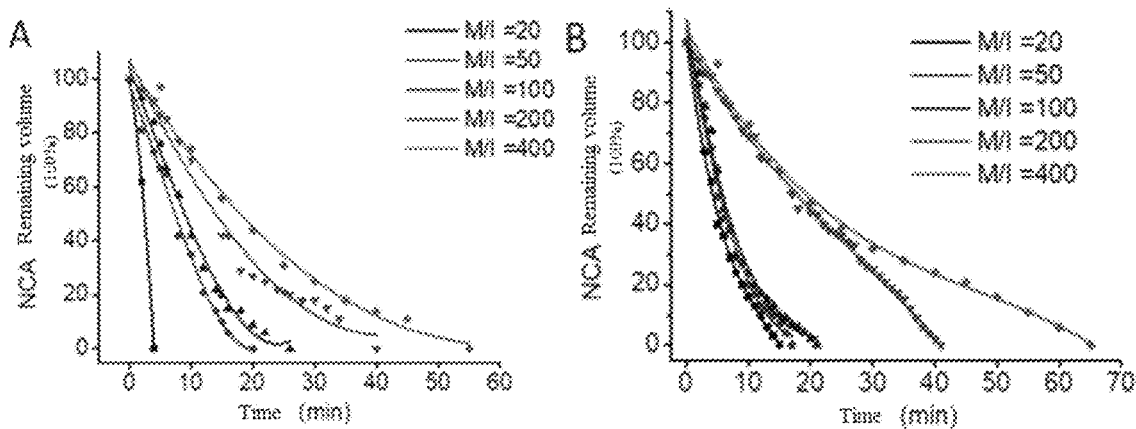

FIG. 6 shows the polymerization rate of polymer A (M/I=20, 50, 100, 200, 400) in Example 3 at the starting concentrations of γ-(4-propyloxybenzyl)-L-glutamic acid-N-carboxylic anhydride monomer of 50 mM and 100 mM, respectively. The polymerization was completed within 10, 20, 30, 40, and 60 min for polymer A with initial monomer concentration of 50 mM and dichloromethane as the reaction solvent, and within 15, 20, 30, 50, 50, 100, 200, and 70 min for polymer A with initial monomer concentration of 100 mM and dichloromethane as the reaction solvent, respectively. Dimethylformamide was used as the reaction solvent for 72 h, and the polymerization rate was increased by 61 to 432 times.

Figure 7:
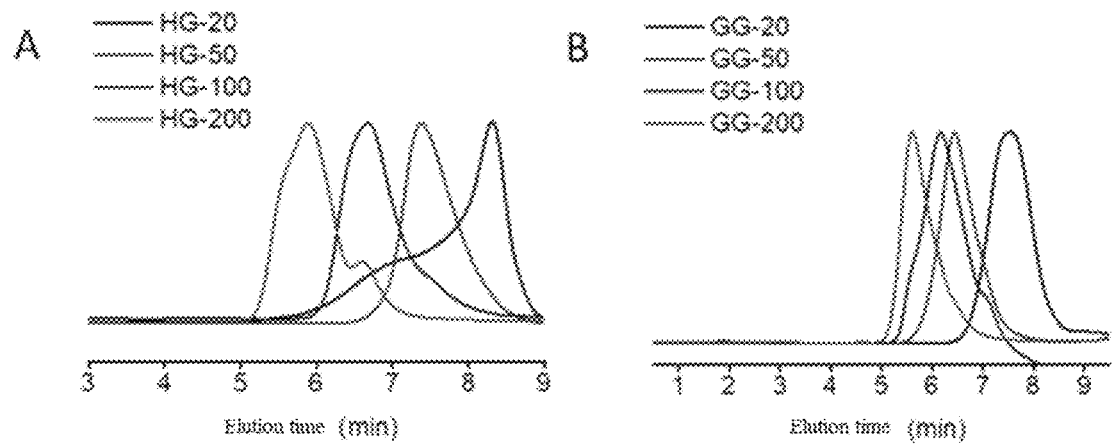
FIG. 7 shows the GPC spectra of polymers, where

FIG. 7 shows the GPC spectra of polymers, where FIG. 7A shows the GPC spectra of polymers in Control Example 1 (M/I=20, 50, 100, 200), using the graph for data analysis, Example 3 possesses molecular weights of about 50 kg/mol, 190 kg/mol, 460 kg/mol, and 640 kg/mol, respectively; while Control Example 1 possesses molecular weights of 8 kg/mol, 24 kg/mol, 34 kg/mol, and 65 kg/mol, respectively.

FIG. 8 shows the particle size diagram of cationic polypeptide, where FIG. 8A shows the particle size diagram of cationic polypeptide in Control Example 1 (M/I=20, 50, 100, 200). From FIG. 8, it can be found that although the cationic polypeptide in Example 3 has a larger molecular weight, its particle size can still be maintained at from 50 to 150 nm.

Figure 9:
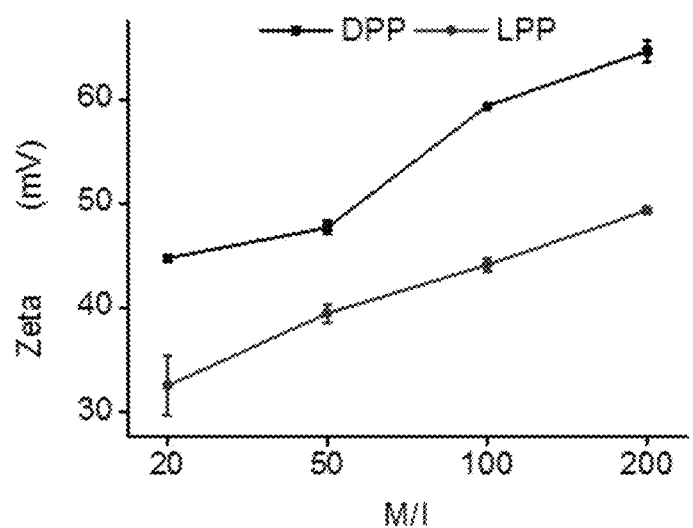
FIG. 9 is the potential diagram of the cationic polypeptide in Example 3 and Control Example 1 (M/I=20, 50, 100, 200); where LPP means: the cationic polypolypeptide in Control Example 1; DPP means: Example 3 Medium cationic polypeptide.

FIG. 9 is the potential diagram of the three-dimensional spherical α-helical cationic polypeptide in Example 3 and Control Example 1 (M/I=20, 50, 100, 200); according to data analysis, the polypeptide of the present invention has a higher positive charge, about 40-70 mV.

Figure 10:
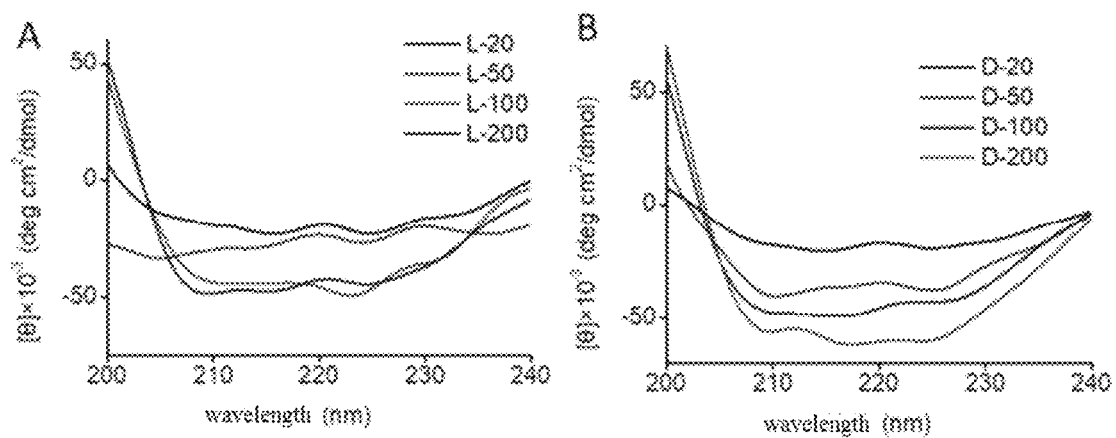
FIG. 10A is a circular dichroism chart of the cationic polypeptide in Control Example 1 (M/I=20, 50, 100, 200)
FIG. 10B is a circular dichrograph of the cationic polypeptide in Example 3 (M/I=20), 50, 100, 200)
Figure 11:
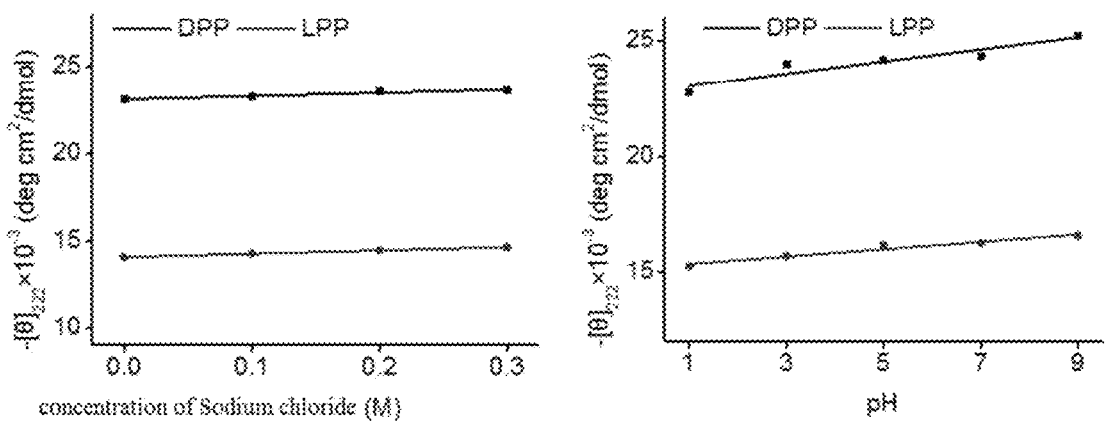
FIG. 11 is a circular dichroism chromatogram (M/I=20, 50, 100, 200) of the conformational stability of the cationic polypeptide in Example 3 and Control Example 1 under different sodium chloride concentrations and different pHs.

FIG. 10 is the circular two chromatogram (M/I=20, 50, 100, 200) of the three-dimensional spherical α-helix cationic polypeptide in Example 3 and Control Example 1 (M/I=20, 50, 100, 200). It is found from FIG. 10 that the polypeptide of the present invention has high helicity, about from 36% to 82%. According to the circular dichroism chart (M/I=20, 50, 100, 200) of the conformational stability of the three-dimensional spherical α-helix cationic polypeptide in Example 3 of FIG. 11 and Control Example 1 under different sodium chloride concentrations (M/I=20, 50, 100, 200). According to data analysis, the α-helical conformation of the polypeptide of the present invention is relatively stable under different sodium chloride concentrations. From the three-dimensional spherical α-helical cationic polypeptide in Example 3 and the circular dichroism chart of the conformational stability of Control Example 1 at different pH (M/I=20, 50, 100, 200). According to data analysis, the polypeptide of the present invention The α-helix conformation of the polypeptide is relatively stable at different pH.

Control Example 1

In a glove box, the γ-(4-propargyloxybenzyl)-L-glutamic acid N-carboxyanhydride monomer of Example 1 was dissolved in anhydrous N,N-dimethylformamide, and then hexamethyldisilazane (initiator) and 1,5,7-triazabicyclo[4.4.0]dec-5-ene were added and stirred at room temperature for 72 h and then precipitated with ice methanol to obtain the intermediate product; if Using anhydrous dichloromethane to replace anhydrous N,N-dimethylformamide, the corresponding intermediate product polymerization degree can be obtained after 72 h reaction, but there is no polymerization acceleration effect mentioned above, that is, the intermediate product polymerization degree obtained by reaction for 1 h is too low (less than 5), unable to continue to use.

When M/I=20, 50, 100, 200, the intermediate products of Control Example 1 have molecular weights of 8 kg/mol, 24 kg/mol, 34 kg/mol, and 65 kg/mol, respectively.

In a glove box, the intermediate product (20 mg, 0.072 mmol alkynyl) was dissolved in DMF, the small azidoguanidine molecule (0.144 mmol) and pentamethyldiethylenetriamine (15 μL, 0.072 mmol) was added, followed by adding cuprous bromide (2 mg, 0.0144 mmol), stirring at room temperature for 48 hours in the glove box; after the reaction is over, take it out of the glove box, open the lid and stir for 20 minutes, added 1 mL of 1M hydrochloric acid, and dialyze with water for 3 days (molecular weight It is 3500 Da) and freeze-dried to obtain a cationic polypeptide. This cationic polypeptide, as a positive control, has the following chemical structure.

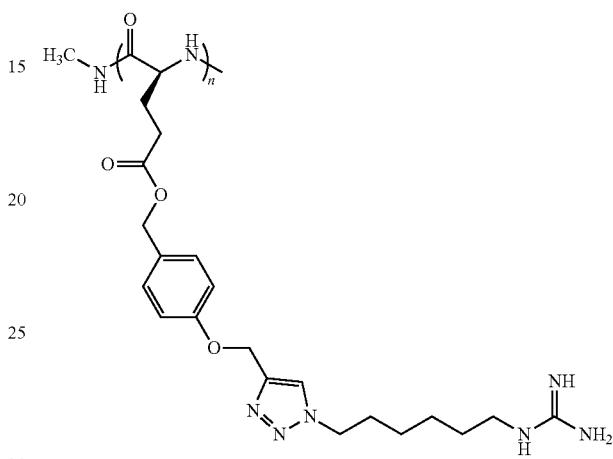

Example 4

The tricationic polypeptide of the example was used as a gene carrier for the preparation, characterization and performance of photothermal-gene combined therapy of breast cancer cells. Prepared an ultrapure water solution with a concentration of 1 mg/mL of cationic polypeptide and a methanol solution with a concentration of 10 mg/mL of indocyanine green, mix 30 μL of indocyanine green with 1 mL of cationic polypeptide, stir for 24 h at room temperature, and then remove the methanol and free indocyanine green by ultrafiltration to obtain complex 1.

The DEPC aqueous solutions of complex 1 and siPKM2 (purchased from Gemma Gene (Shanghai, China)) were prepared at concentrations of 1 mg/mL and 0.1 mg/mL, respectively. Mix according to different mass ratios of compound 1/siPKM2 (8/1, 10/1, 12/1, 15/1 and 20/1), vortex for 10 seconds and incubate at room temperature for 30 minutes, and form compound 1 by electrostatic adsorption/siPKM2 complex, i.e., complex 2.

Mix human serum albumin and complex 2 in different mass ratios (1/4, 1/2, 1/1, 2/1 and 4/1), vortex for 10 seconds and incubate at room temperature for 30 minutes to form a complex 3; The FAM-siRNA (purchased from Gemma Gene (Shanghai, China)) and the three polypeptides of the example and the Control Example one polypeptides were used in different mass ratios (1/5, 1/10, 1/15) And 1/20) mix, vortex for 10 seconds and incubate at room temperature for 30 minutes to form complex 4. In addition, FAM-siRNA is mixed with PEI at 1/5, and LPF at 1/2, vortexed for 10 seconds and incubated at room temperature 30 minutes, the formed complex is used as a control; load complex 2 into the 2% agarose gel electrophoresis loading hole, run at 120 V for 20 minutes, ethidium bromide staining display, gel imaging system imaging, determination Encapsulation efficiency of siRNA. Use dynamic light scattering (DLS) to determine the particle size distribution of complex 3: Incubate complex 2 and complex 3 in a phosphate buffer containing 10% FBS for different times to monitor the change in particle size to evaluate complex 2 and the stability of complex 3 in serum; MCF-7 cells were seeded into 96-well plates at 2×104 cells per well, and then cultured in DMEM medium containing 10% FBS for 24 hours. Then the medium was replaced with serum-free DMEM, complex 4 was added to the well at 0.1 µg FAM-siRNA per well, and incubated for 4 h. Rinse 3 times with buffer containing heparin sodium, added RIPA lysis solution (100 µL) to lyse, measure the content of FAM-siRNA ($\lambda$ex=480 nm, $\lambda$em=530 nm) with a microplate reader, and measure the cells with BCA kit The internal protein content was used to study the cell uptake efficiency of complex 4; MCF-7 cells were seeded into a 96-well plate at 2×104 cells per well, and then cultured in DMEM medium containing 10% FBS for 24 hours. Change to serum-free DMEM medium, added the mixed solution of polypeptide (2 µg/well) and fluorescein isothiocyanate (1 µg/well) in Example 3, incubate for 2 h, and rinse with PBS containing heparin sodium Three times, RIPA lysis solution (100 µL) was lysed, and finally the fluorescence intensity of FITC was measured with a microplate reader ($\lambda$ ex=480 nm, $\lambda$ em=530 nm), and the BCA kit was used to determine the intracellular protein content to explore Example 3 perforation ability of midpolypeptide; use confocal laser scanning microscope to observe the escape of endosomes in complex 4. MCF-7 cells were seeded into a glass-bottom culture dish (15 mm) at a density of 2×104 cells/well, and then cultured in DMEM medium containing 10% FBS for 24 hours. Change to serum-free DMEM medium, added complex 4 (w/w=15, 1 µg FAM-siRNA/well), and incubate for 4 h. Rinse with buffer containing heparin sodium 3 times, stain with Hoechst (5 µg/mL) and Lysotracker Red (200 nM) for 30 min and 1 h, respectively, and observe under a confocal laser scanning microscope. Use ImageJ to calculate the colocalization rate of FAM-siRNA and Lysotracker Red.

MCF-7 cells were seeded into a 96-well plate at 8000 cells per well, and then cultured in DMEM medium containing 10% FBS for 24 hours. Then change to serum-free DMEM medium, added different concentrations of complex 3, incubate for 24 h, change the medium, irradiate the cells with a 808 nm light source for 5 min (0.5 W/cm$^2$ or 1 W/cm$^2$), and continue to incubate for 24 h. Finally, the MTT method was used to detect the cell viability.

Female Balb/C mice (18-20 g) bearing MCF-7 tumor in situ (200 mm$^3$) were injected with complex 4 (siRNA 1.25 mg/kg; ICG 2.25 mg/kg) through the tail vein. After 24 hours of administration, half of the mouse tumors were irradiated with a light source of 808 nm (0.8 W/cm$^2$, 5 min). The mice were sacrificed 24 hours later, and the tumors were collected. Homogenize 30 mg of tumor-extracted RNA with 1 mL of TRIZOL reagent, and homogenize 60 mg of tumor-extracted protein with 1 mL of lysis buffer. Use real time-PCR, Westernblot and immunofluorescence technology to study gene transfection efficiency in vivo.

Figure 12:
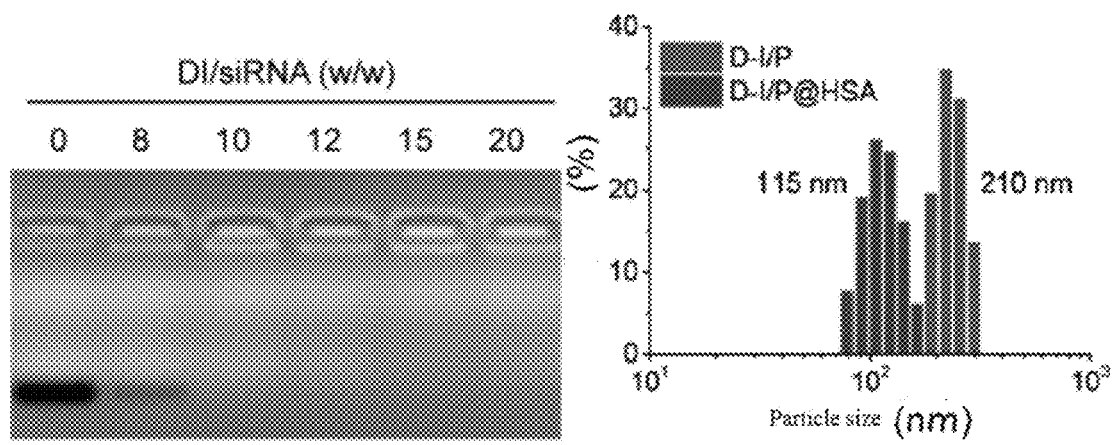
FIG. 12 is the gel electrophoresis diagram of the compound 2 in Example 4 under different mass ratios; DI/siRNA means: the particle size distribution diagram of the compound 2 in Example 4; the compound 2 and the compound 3; where, DI/P means: complex 2, DI/P@HSA means: complex 3.

FIG. 12 is a gel electrophoresis diagram of the compound 2 under different mass ratios in Example 4. According to data analysis, when the mass ratio is greater than or equal to 10, the compound 2 can completely encapsulate the siRNA. From the particle size distribution diagrams of complex 2 and complex 3 in FIG. 19, it is determined that the optimal mass ratio of HSA to the cationic polypeptide in Example 3 is 1/1.

Figure 13:
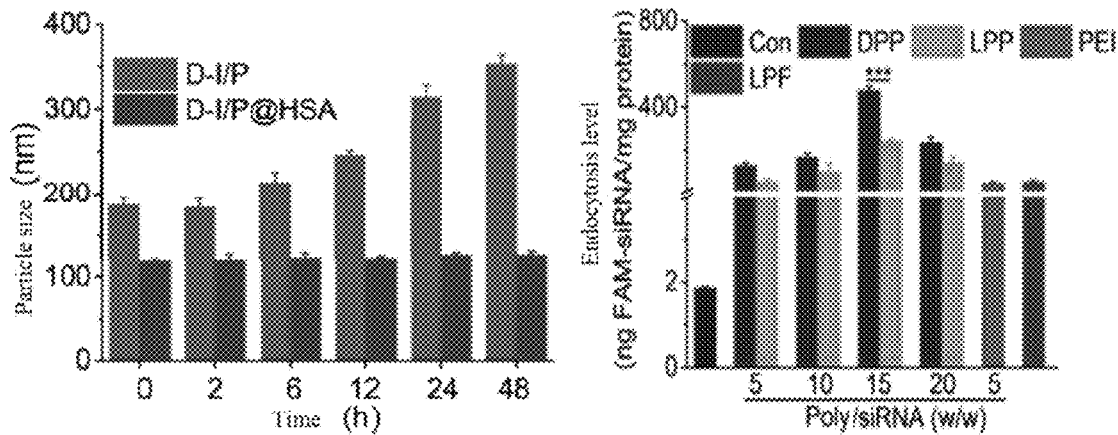
FIG. 13 is a graph showing the changes in the particle size of complex 2 and complex 3 in serum; the uptake level of complex 4 by MCF-7 cells; wherein, Poly/siRNA represents a mass ratio of complex 4, polymerized polypeptide to nucleic acid molecule, Con: control group.

FIG. 13 shows the changes in the particle size of complex 2 and complex 3 in serum. Data analysis shows that the particle size of complex 3 can remain stable within 48 hours, indicating that human serum albumin can improve the serum stability of the complex. From the graph of the uptake level of complex 4 by MCF-7 cells. It can be seen that the cell uptake efficiency of complex 4 is 2 times higher than that of the related complex of Control Example 1.

Figure 14:
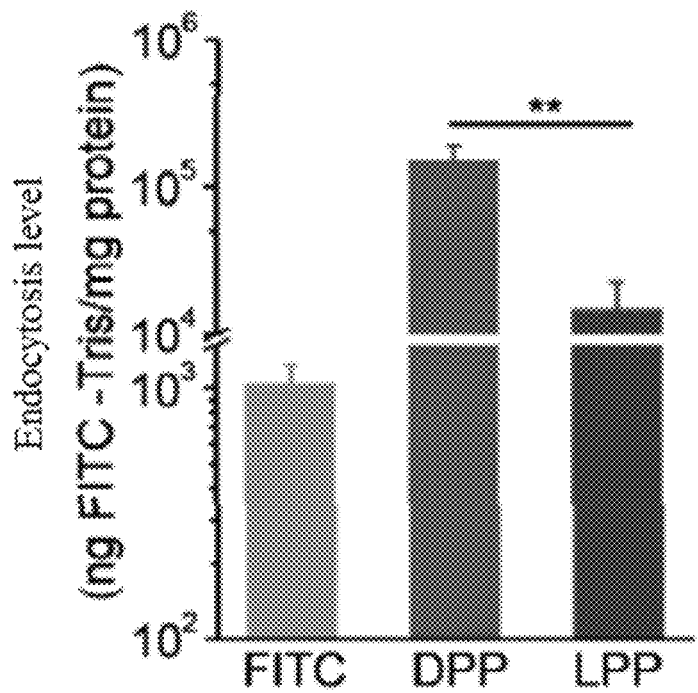
FIG. 14 is a graph showing the uptake level of fluorescein isothiocyanate by MCF-7 cells.

FIG. 14 is a graph of the uptake level of fluorescein isothiocyanate by MCF-7 cells, representing the transmembrane activity of the polypeptide in Example 3 and Control Example 1. The data shows that the polypeptide in Example 3 has stronger penetration Membrane capacity.

Figure 15:
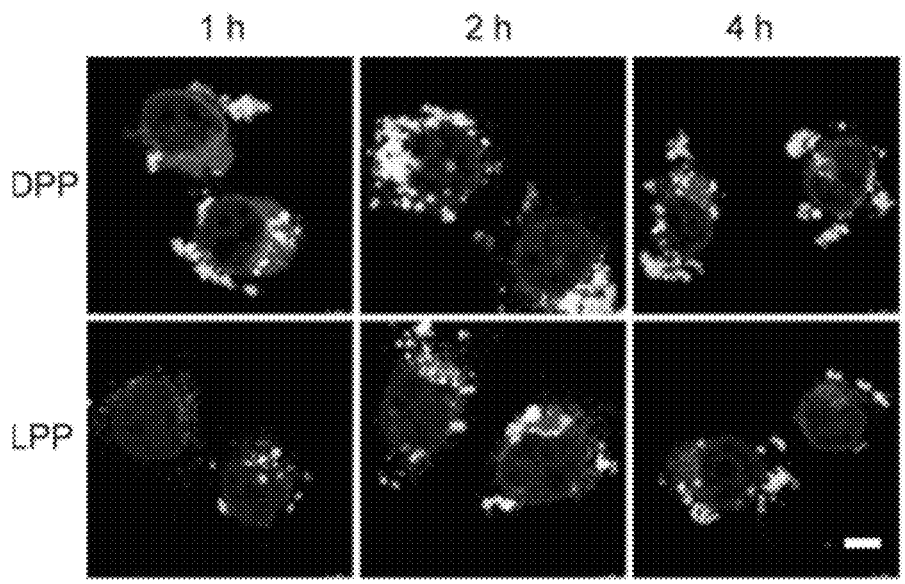
FIG. 15 is a diagram showing the escape of inclusion bodies/lysosomes of the complex on MCF-7 cells.

FIG. 15 shows the escape of inclusion bodies/lysosomes of the complex on MCF-7 cells. The co-localization rates of the complex are ~20% and ~32%, respectively, indicating that the polypeptide of Example 3 can achieve high-efficiency lysis. The enzyme body escaped, and its escape ability was better than the monopolypeptide of the Control Example.

Figure 16:
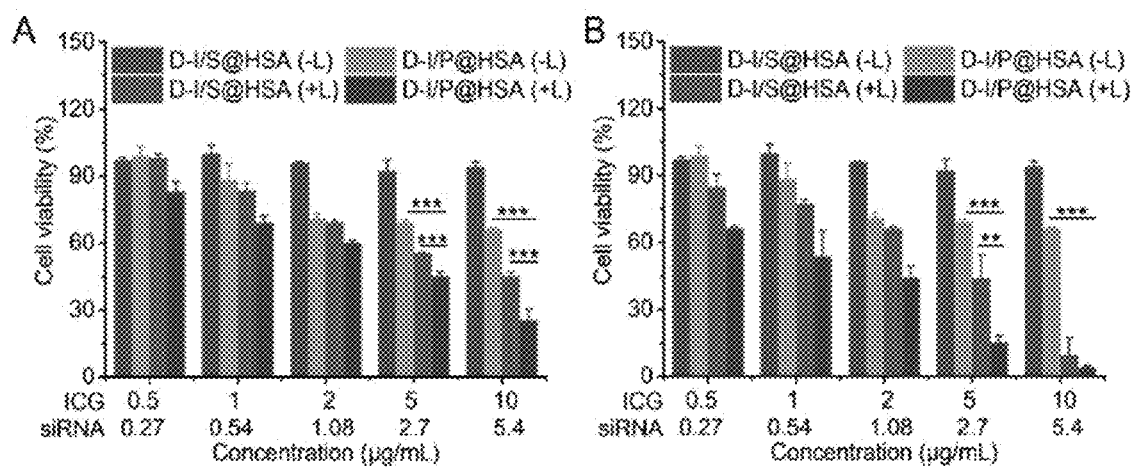
FIG. 16 is the cytotoxicity diagram of complex 3 on MCF-7 cells; among them, A: on MCF-7 cells, the cytotoxicity diagram of complex 3 on 808 nm, 0.5 W/cm$^2$, 5 min.; B: The cytotoxicity diagram of complex 3 on MCF-7 cells under the light conditions of 808 nm, 1 W/cm$^2$, 5 min; (+L) means: light, (−L) means: no light; DI/S@HSA: The complex of cationic polymer and indocyanine green, nonsense RNA siScr and human serum albumin in Example 3, DI/P@HSA: complex 3.

FIG. 16 shows the cytotoxicity of complex 3 on MCF-7 cells. It can be seen from FIG. 16 that the PKM2-mediated tumor starvation of complex 3 enhances photothermal ablation, and its anti-tumor effect is significantly better than that of single photothermal therapy or Hunger treatment.

Figure 17:
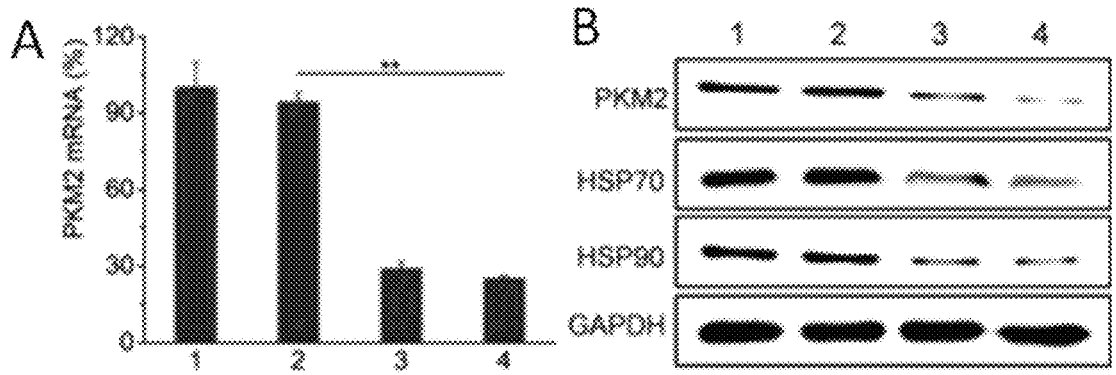

FIG. 17 shows the gene silencing efficiency and heat shock protein inhibition efficiency of female Balb/C mice bearing MCF-7 tumor in situ. The transfection efficiency of complex 3 can down-regulate the level of PKM2 mRNA by 70% in the presence or absence of light. It proves the advantages of the polypeptide of Example 3 in gene delivery; in addition, complex 3 can effectively reduce the expression of PKM2 protein, and ultimately inhibit the production of downstream metabolites such as heat shock protein.

The invention claimed is:

1. A three-dimensional spherical α-helical polypeptide with high gene delivery efficiency, having a chemical structure of Formula (1):

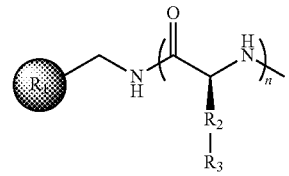

in Formula (I), R₁ is a dendrimer polyacrylamide unit selected from the group consisting of:
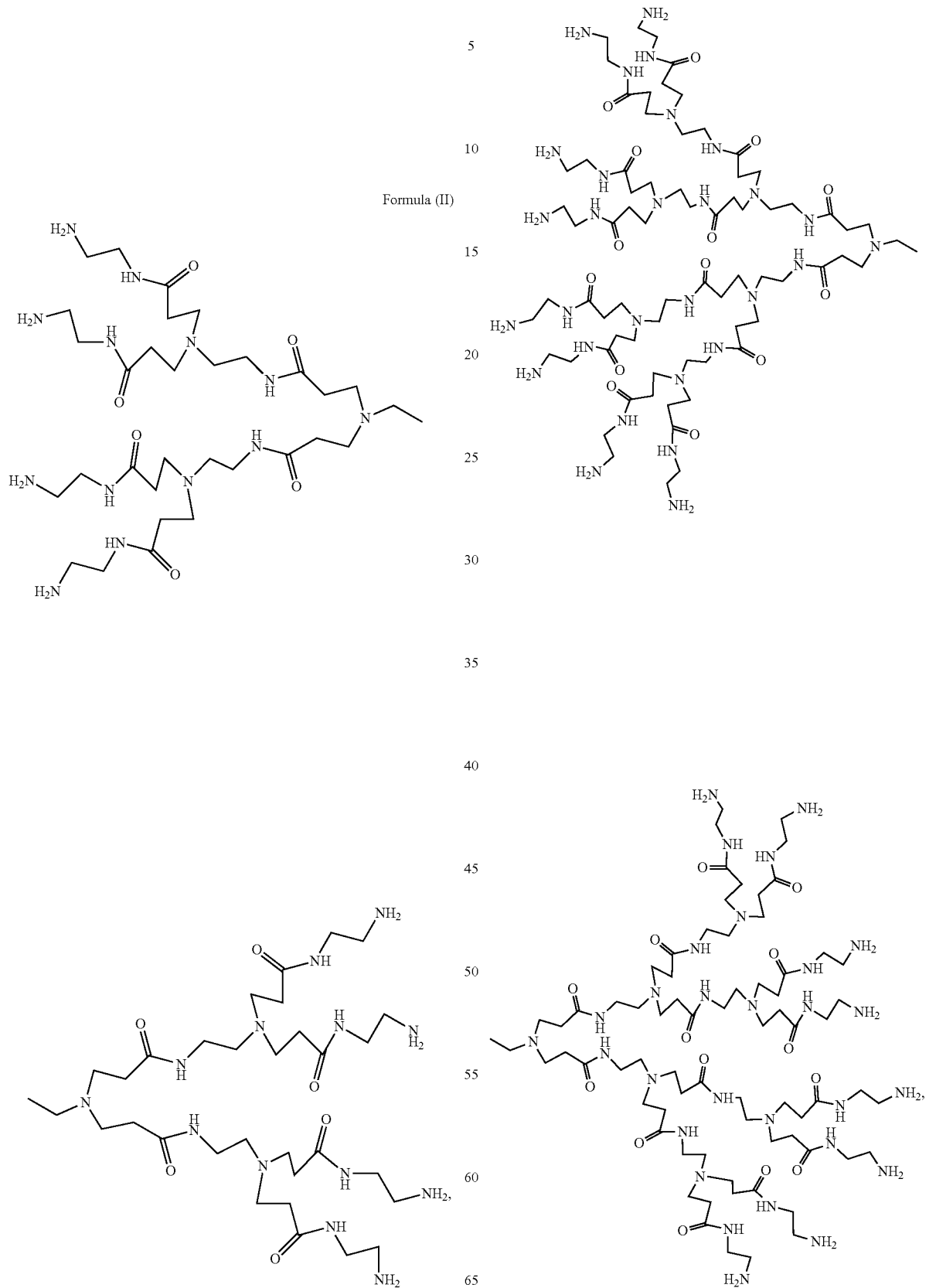

Formula (VI)
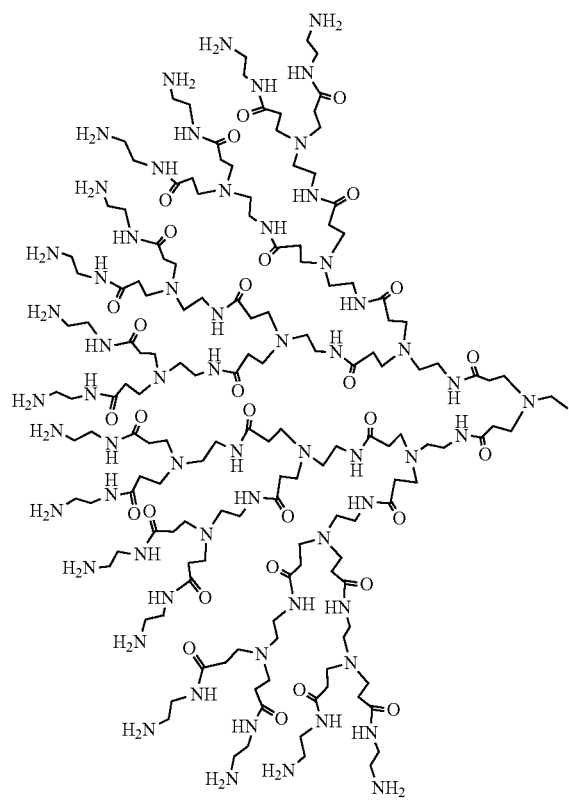
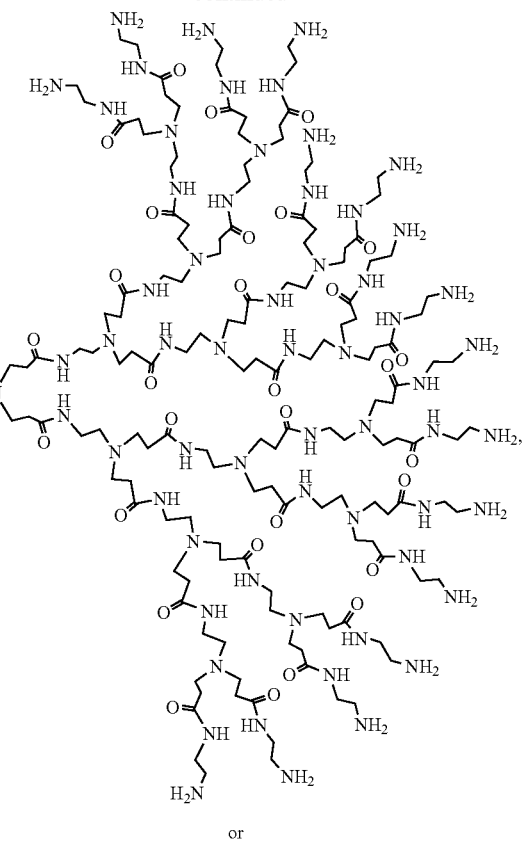
-continued
or

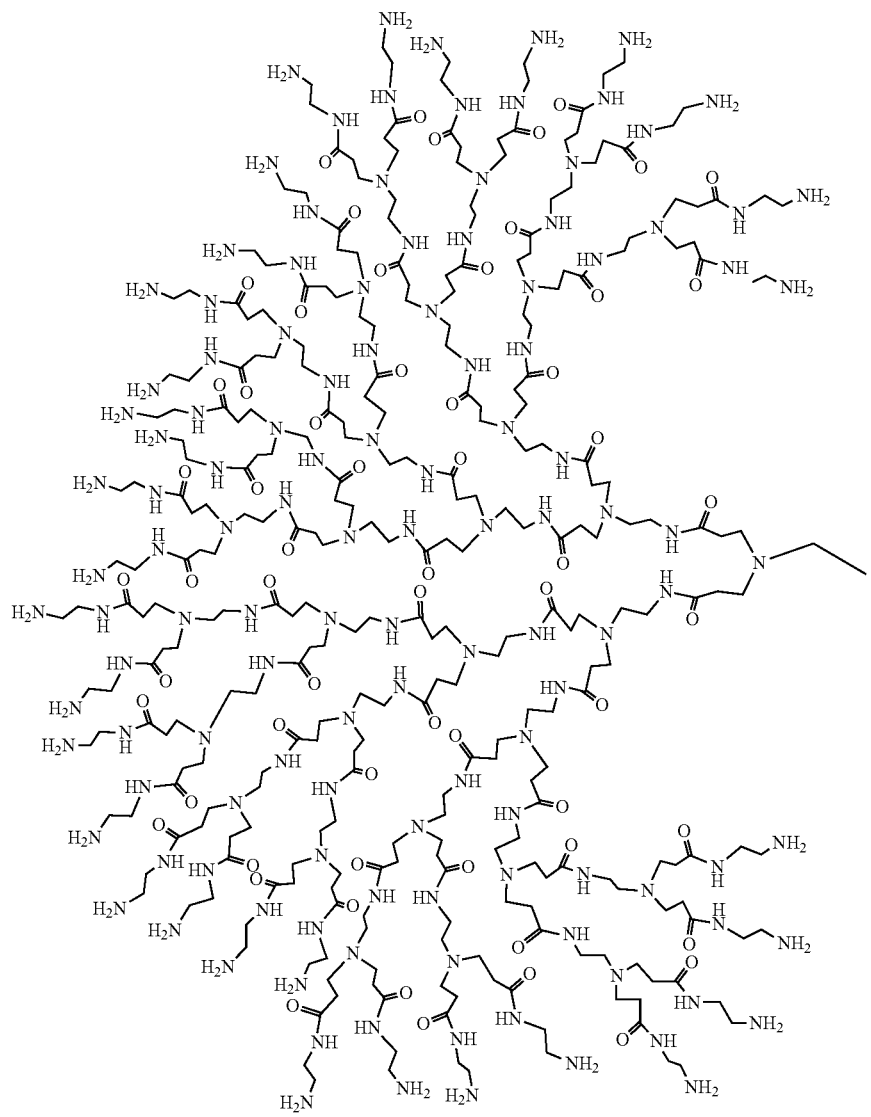
Formula (V)

-continued

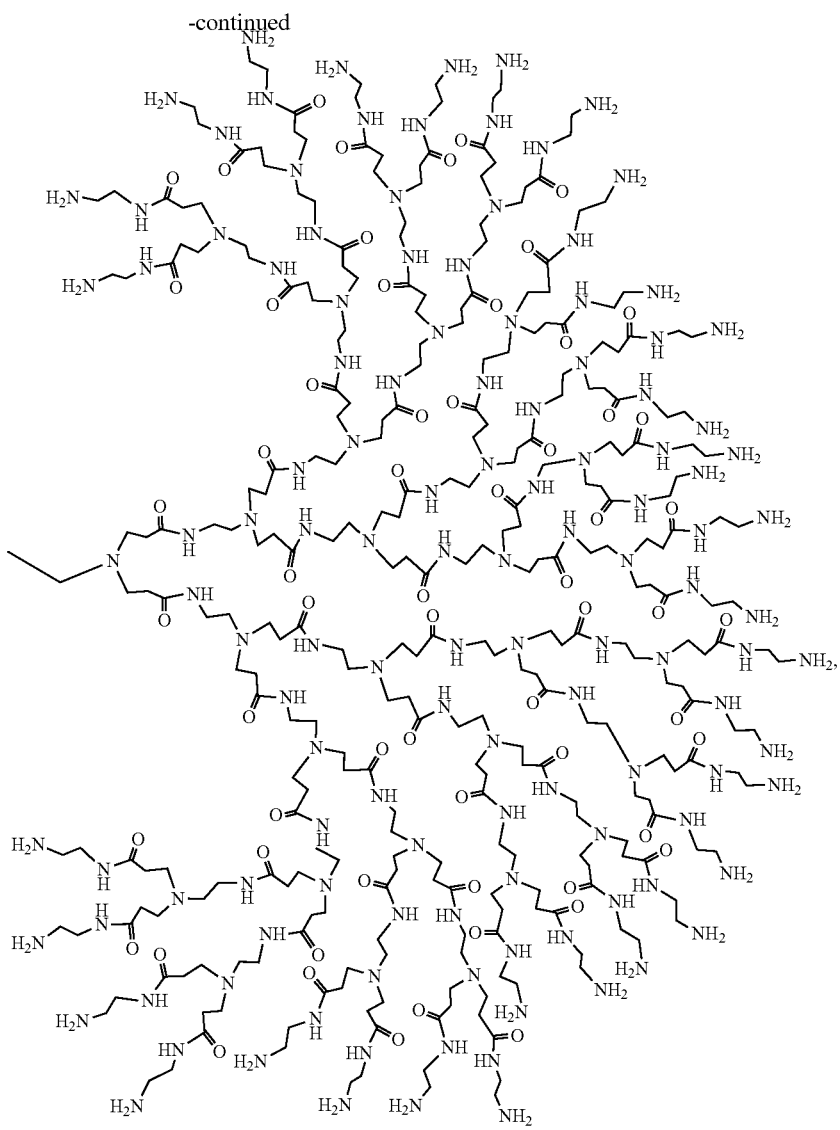

$R_2$ is N-carboxylic anhydride monomer unit, $R_3$ is an electrical small molecular unit selected from the group consisting of

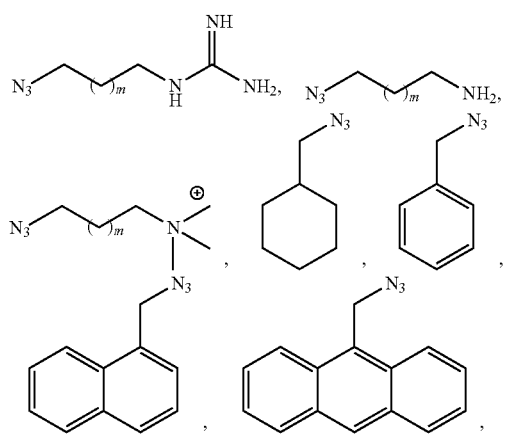

-continued

[structures: pyrene-CH2-N3, biphenyl-CH2-N3, or succinic anhydride]

wherein m is from 1 to 6, and
wherein n is from 20 to 200.

2. The three-dimensional spherical α-helical polypeptide of claim 1, characterized in that a method of preparing the three-dimensional spherical α-helical polypeptide comprises the following steps: initiating a polymerization reaction of an N-carboxyanhydride compound by a branched dendrimer polyacrylamide to obtain an intermediate; and then reacting the intermediate with an electrical small molecule to obtain the three-dimensional spherical α-helical polypeptide with high gene delivery efficiency.

3. The three-dimensional spherical α-helical polypeptide of claim 2, characterized in that the method of preparing the three-dimensional spherical α-helical polypeptide comprises the following steps:
  (1) reacting the N-carboxyanhydride compound with a branched dendrimer polyacrylamide of Formula (II), Formula (III), Formula (IV), or Formula (V) in an organic solvent to obtain the intermediate; the N-carboxyanhydride compound being γ-(4-propargyloxybenzyl)-L-glutamic acid N-carboxyanhydride, γ-propargyl-L-glutamic acid N-carboxyanhydride, or N,N-benzyloxycarbonyl-L-lysine anhydride;
  (2) obtaining the three-dimensional spherical α-helical polypeptide with efficient gene delivery capability by a click chemistry reaction of the intermediate with the electrical small molecule.

4. The three-dimensional spherical α-helical polypeptide with efficient gene delivery capability of claim 3, characterized in that in step (1), when the organic solvent is dichloromethane, the reaction is conducted for 0.5-1 h at room temperature and when the organic solvent is N,N-dimethylformamide, the reaction is conducted for 72 h at room temperature; in step (2), the click chemistry reaction is catalyzed by pentamethyldiethylenetriamine, cupric bromide in step (2), the reaction is catalyzed by pentamethylenediethylenetriamine and copper bromide, and the reaction is conducted at room temperature for 24 h.

5. A preparation method of a three-dimensional spherical α-helical polypeptide, comprising the following steps:
  (1) reacting a branched dendrimer polyacrylamide selected from the group consisting of:

Formula (II)

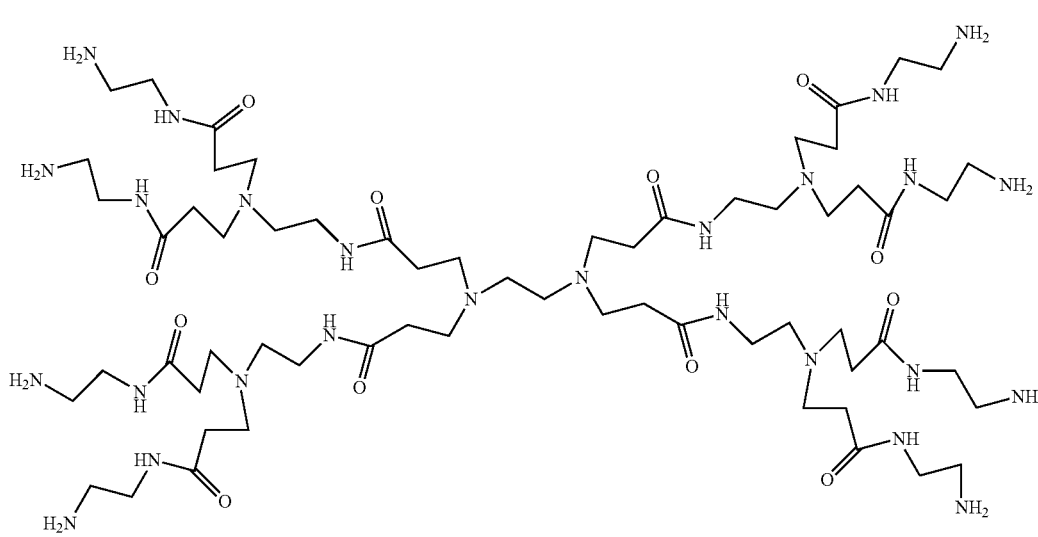

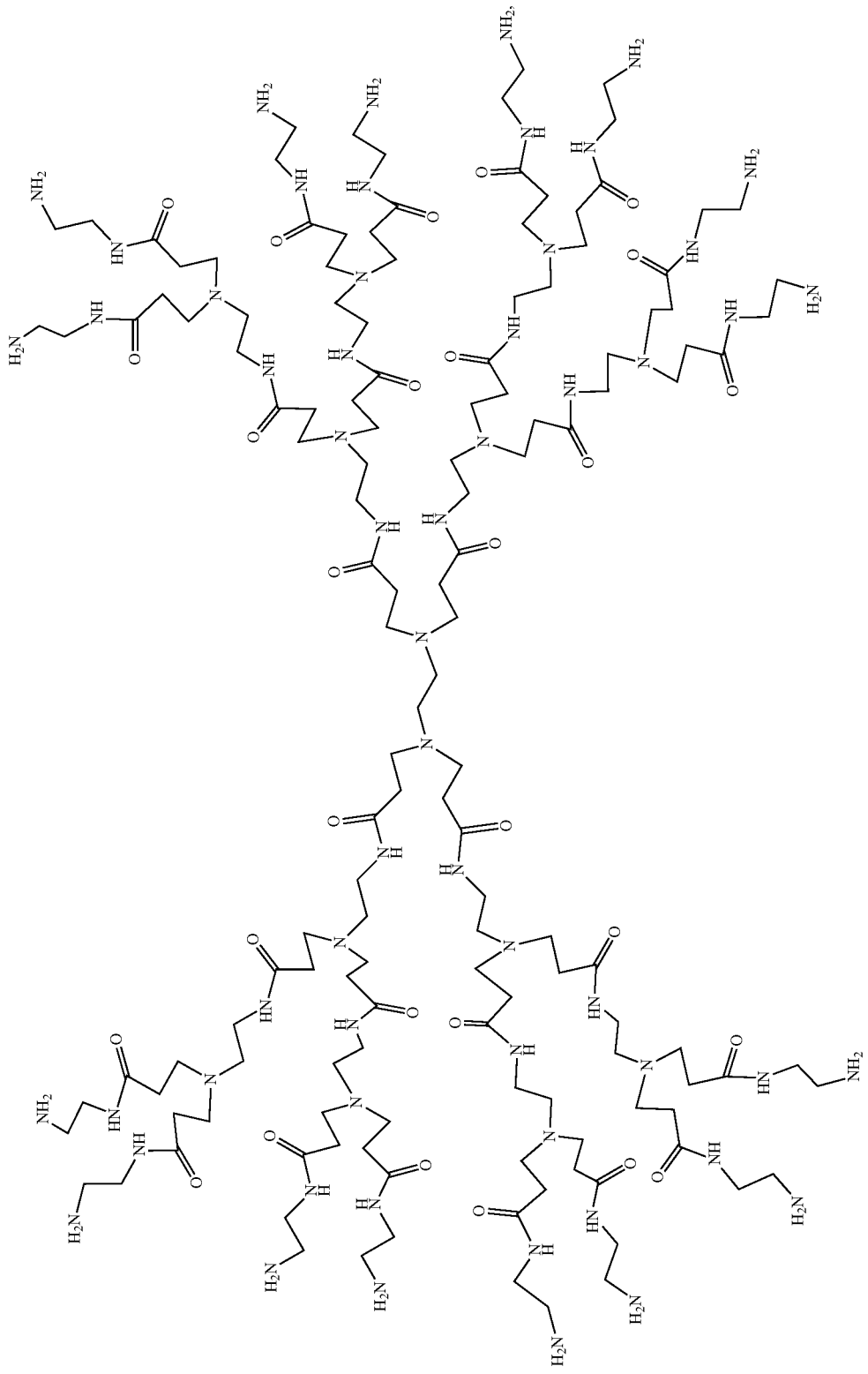
Formula (III)

Formula (VI)
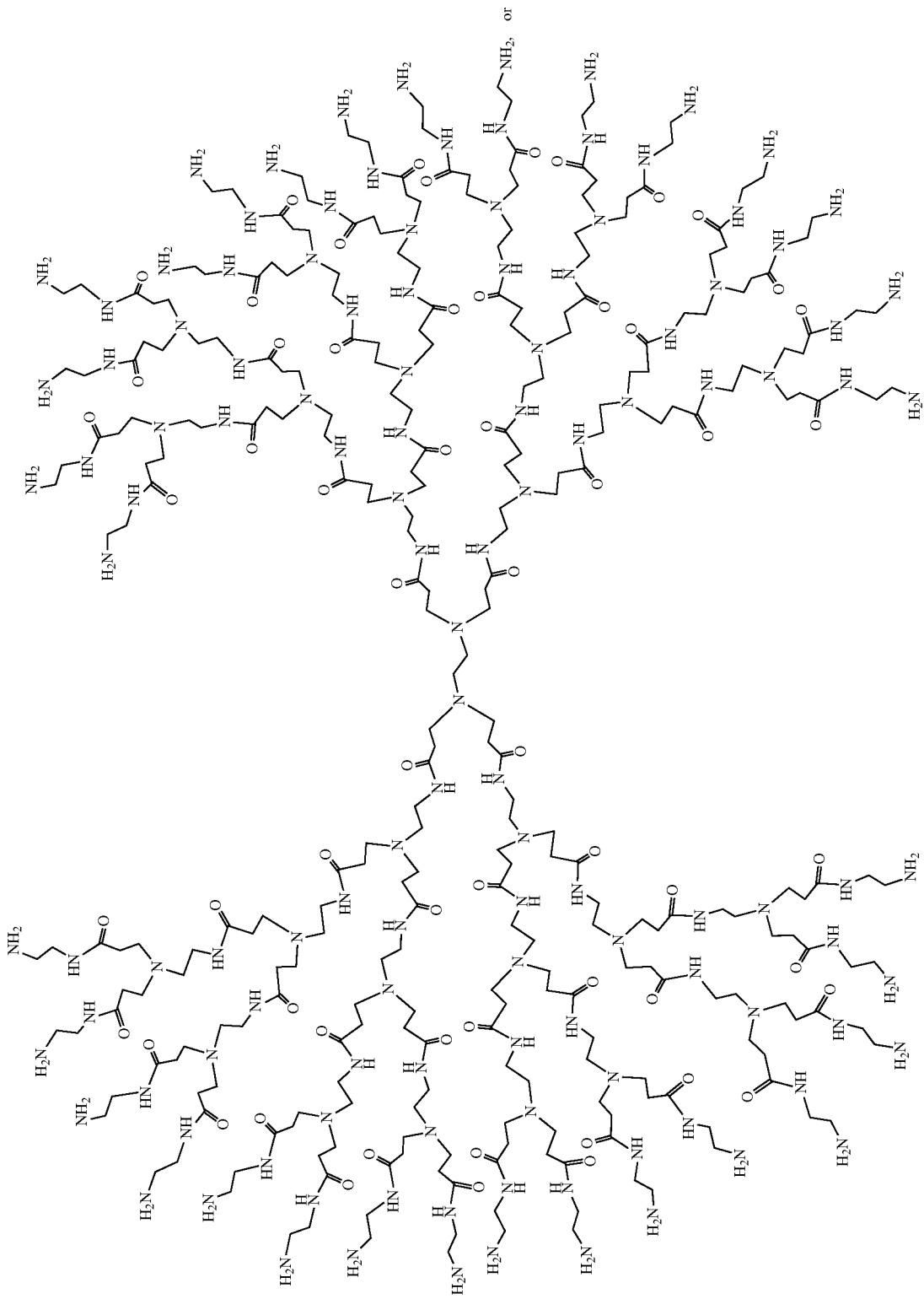
, or

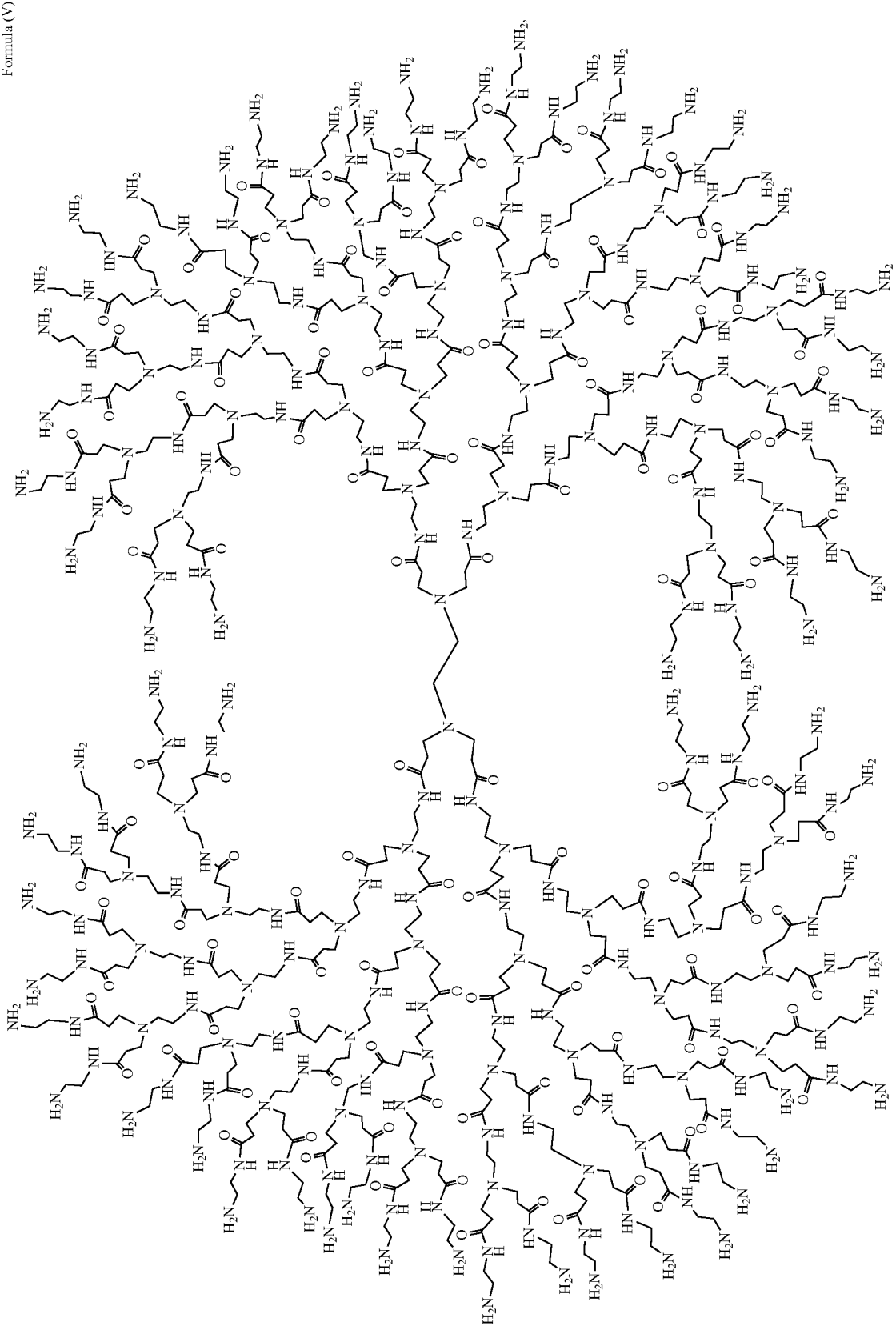
Formula (V)

with an N-carboxyanhydride compound to obtain an intermediate; the N-carboxyanhydride compound being γ-(4-propargyloxybenzyl)-L-glutamic acid N-carboxyanhydride, γ-propargyl-L-glutamic acid N-carboxyanhydride, or N,N-benzyloxycarbonyl-L-lysine anhydride;

(2) conducting a click chemistry reaction of the intermediate with an electrophilic small molecule selected from the group consisting of:

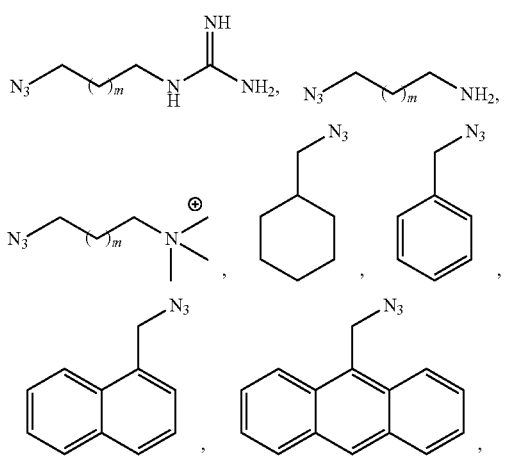

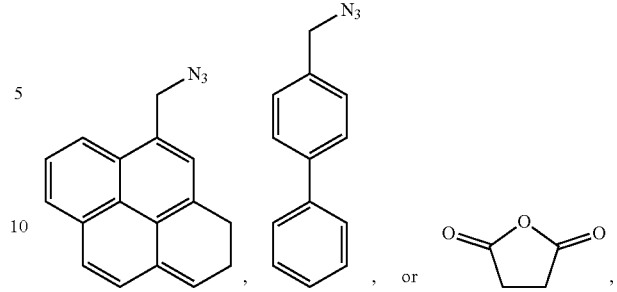

to obtain the three-dimensional spherical α-helical polypeptide with efficient gene delivery capability.

6. A nano-medicine, comprising the three-dimensional spherical α-helical polypeptide with efficient gene delivery capability of claim 1 and a nucleic acid molecule.

7. The nano-medicine of claim 6, wherein the nucleic acid molecule is a DNA, an RNA, an oligonucleotide or a polynucleotide; a mass ratio of the three-dimensional star-shaped α-helical polypeptide to the nucleic acid molecule is (1 to 30):1; a particle size of the nano-medicine is from 100 to 1000 nm; a zeta potential of the nano-medicine is from −20 to 70 mV.

8. An intermediate, characterized in that a method of preparing the intermediate comprises the following steps: (1) reacting an N-carboxyanhydride compound with a branched dendrimer polyacrylamide selected from the group consisting of:

Formula (II)

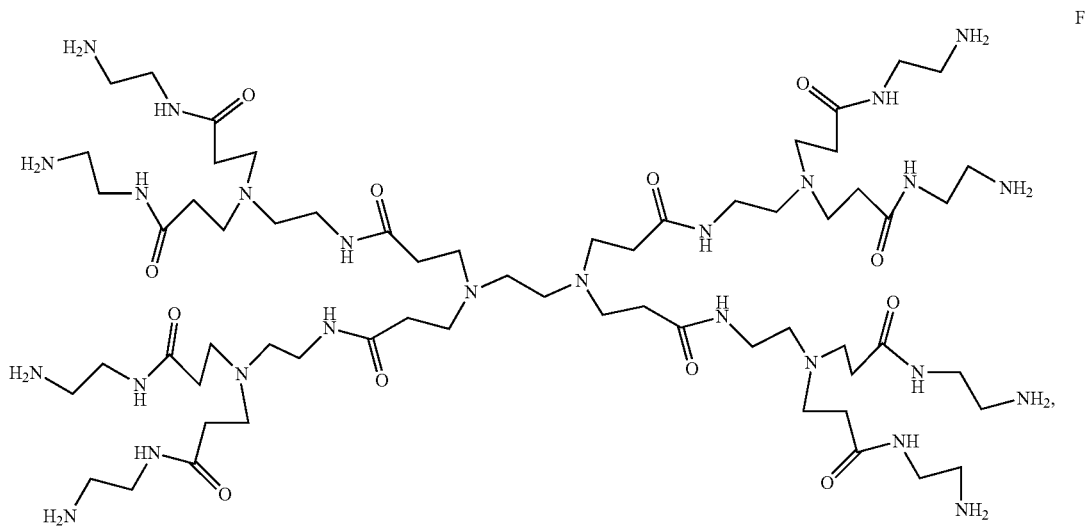

Formula (III)
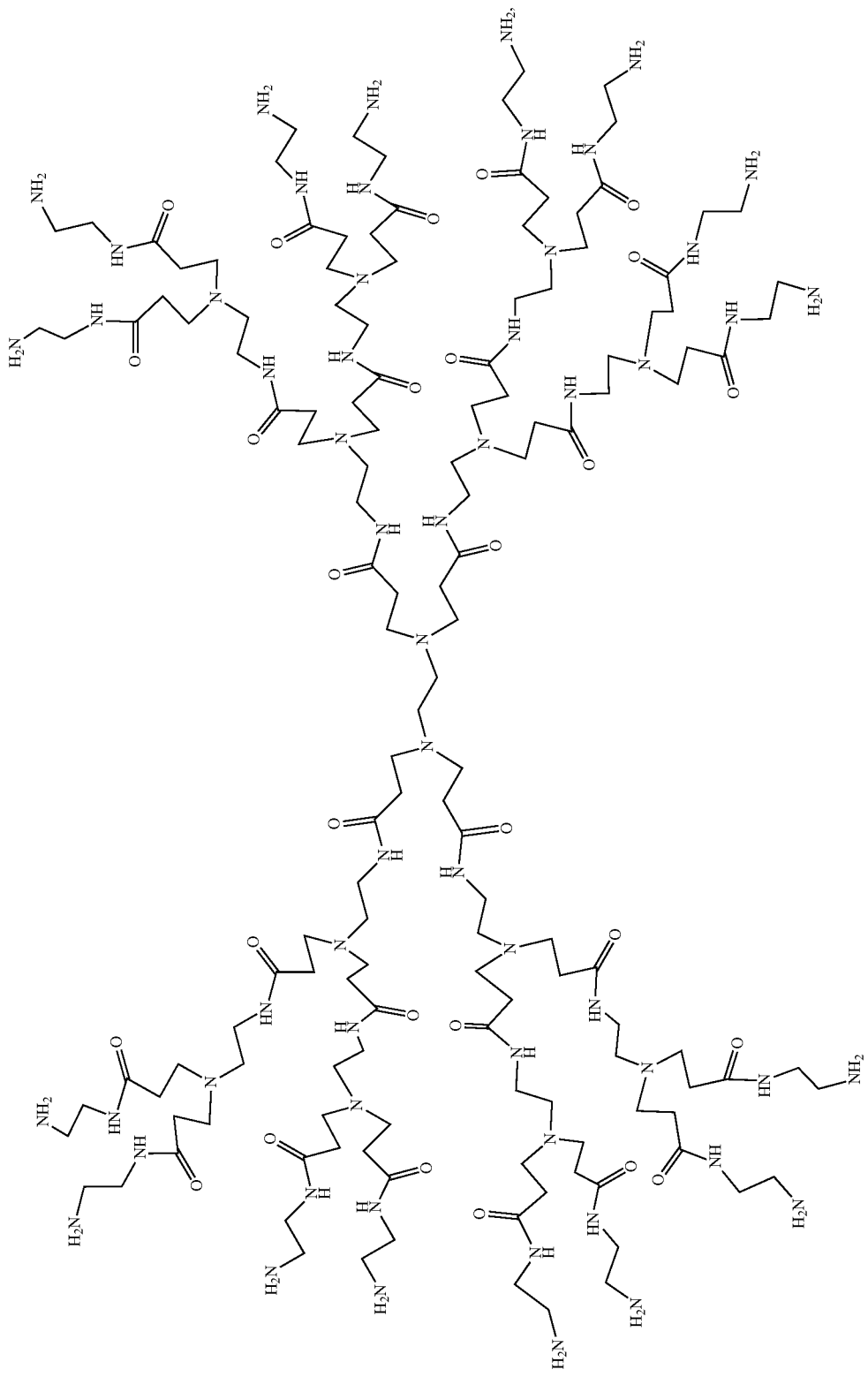

Formula (VI)
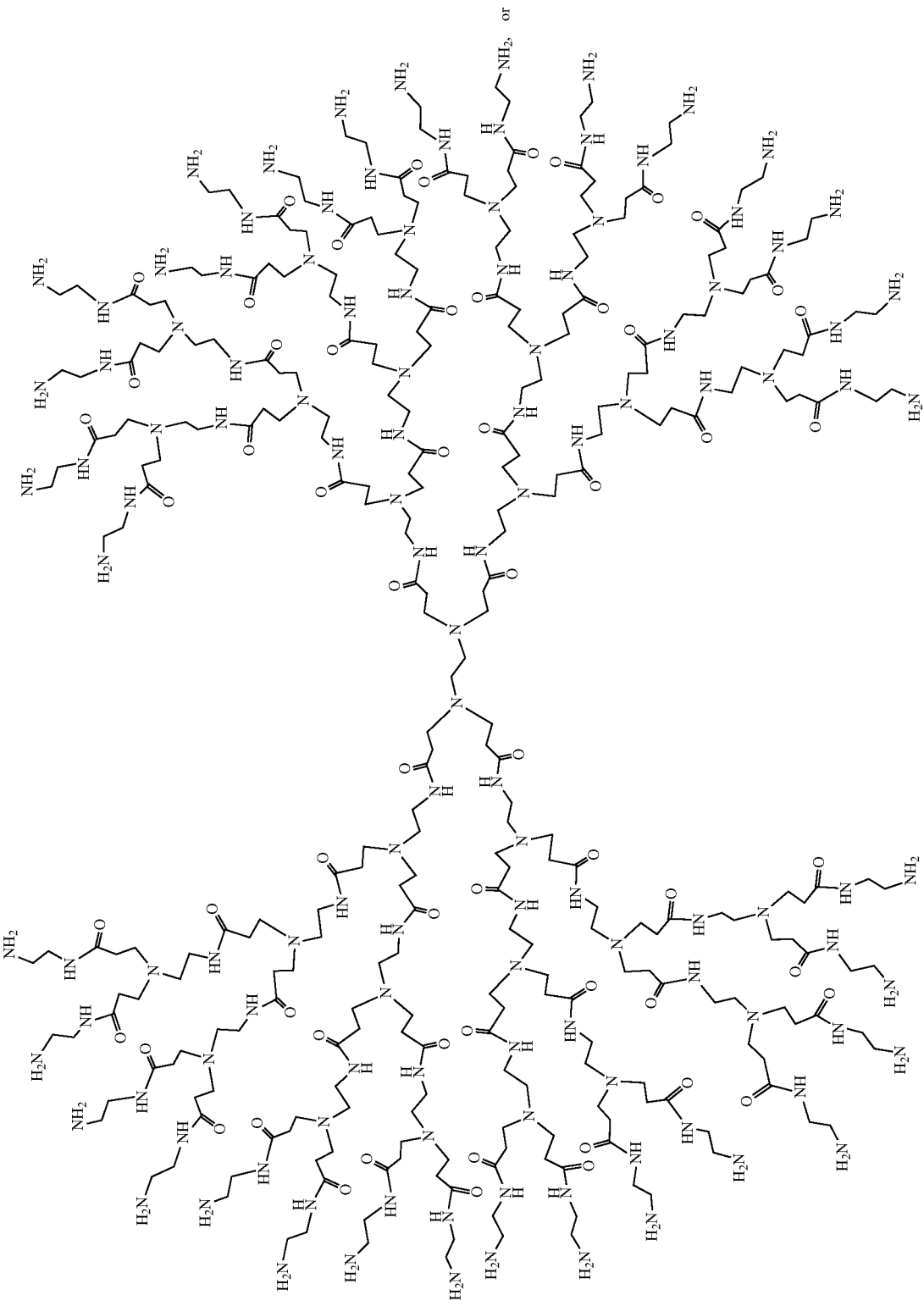
, or

Formula (V)
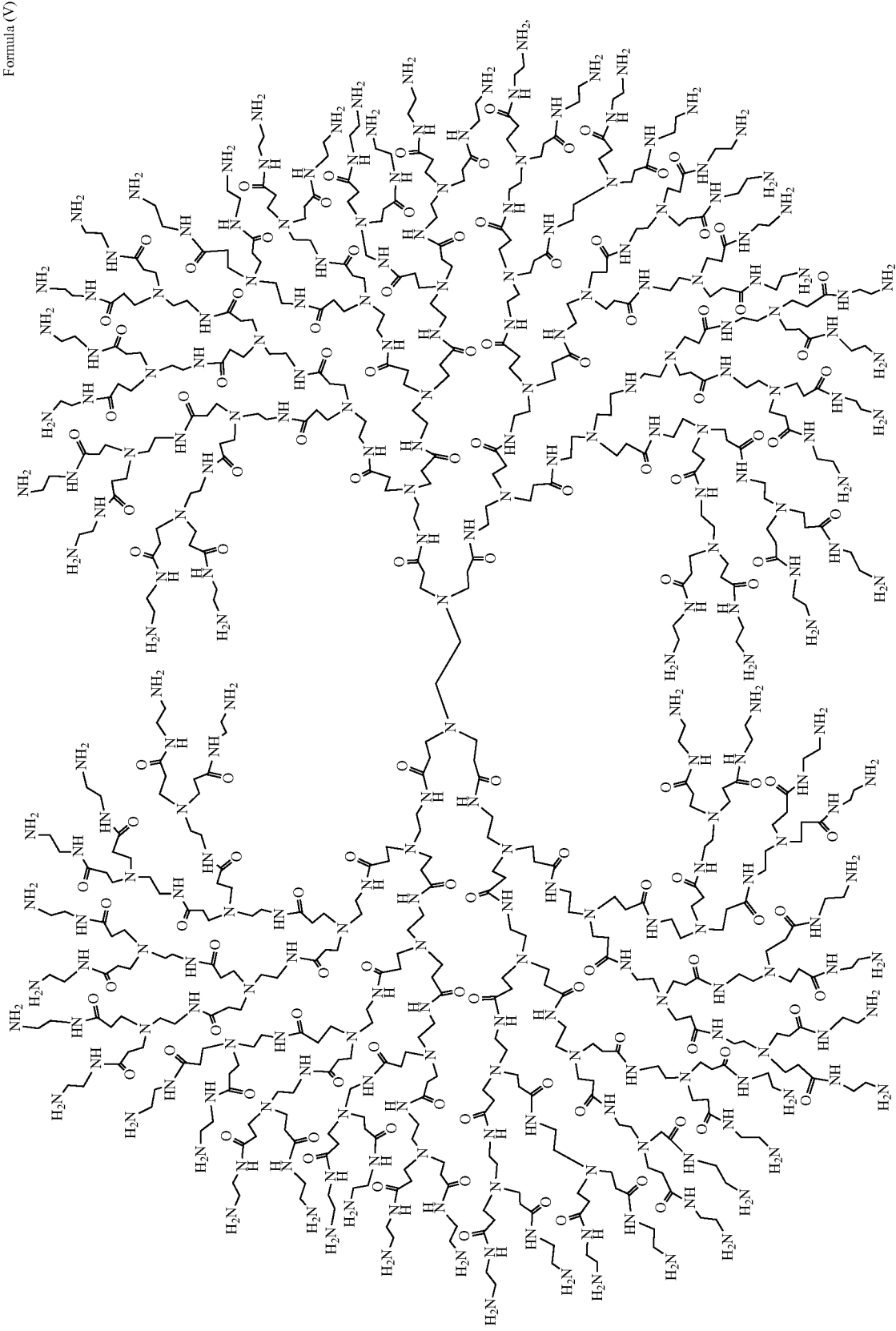

in an organic solvent to obtain the intermediate; the N-carboxyanhydride compound being γ-(4-propargyloxybenzyl)-L-glutamic acid N-carboxyanhydride, γ-propargyl-L-glutamic acid N-carboxyanhydride, or N,N-benzyloxycarbonyl-L-lysine anhydride.

* * * * *